(12) United States Patent
Puentener et al.

(10) Patent No.: US 7,504,544 B2
(45) Date of Patent: Mar. 17, 2009

(54) ASYMMETRIC HYDROGENATION OF 1,1,1-TRIFLUOROACETONE

(75) Inventors: Kurt Puentener, Basel (CH); Pius Waldmeier, Wegenstetten (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/879,644

(22) Filed: Jul. 18, 2007

(65) Prior Publication Data

US 2008/0027249 A1    Jan. 31, 2008

(30) Foreign Application Priority Data

Jul. 27, 2006 (EP) .................. 06117928

(51) Int. Cl.
*C07C 29/14* (2006.01)
(52) U.S. Cl. .............. 568/840; 568/880; 568/881
(58) Field of Classification Search .............. 568/840, 568/880, 881
See application file for complete search history.

(56) References Cited

U.S. PATENT DOCUMENTS

| 5,302,738 A | 4/1994 | Foricher et al. |
| 5,488,172 A | 1/1996 | Cereghetti et al. |

FOREIGN PATENT DOCUMENTS

| EP | 0 398 132 | 11/1990 |
| EP | 580 331 | 1/1994 |
| WO | WO 92/16535 | 10/1992 |
| WO | WO 2005/014563 | 2/2005 |
| WO | WO 2007/006650 | 1/2007 |

OTHER PUBLICATIONS

Douchet et al., Angew. Chem. Int. Ed., vol. 37, No. 12, pp. 1703-1707 (1998).
Ohkuma et al., J. of the American Chem. Society, vol. 124(23) pp. 6508-6509 (2002).
Crawford et al., J. of the Chem. Society, Section C, Organic Chemistry vol. 22, pp. 2332-2333 (1967).
Tang et al., Chemical Reviews, vol. 103, pp. 3029-3069 (2003).
Bucciarelli et al., Synthesis, pp. 897-899 (1983).
Rosen et al., Chimica Oggi, Suppl. 2004, pp. 43-45.
Kuroki et al., Org. Lett. vol. 3, pp. 457-459 (2001).
Noyori et al., Angew. Chem. Int. Ed. vol. 40, pp. 40-73 (2001).
Ohkuma et al., J. Am. Chem. Soc. vol. 127, pp. 8288-8289 (2005).
Sandoval et al., J. Am. Chem. Soc. vol. 125, pp. 13490-13503 (2003).
Lide, D. R., Handbook for Chemistry & Physics, CRC Press, Section 8, p. 8-55 (1994).
Ohkuma et al., J. Am. Chem. Soc. vol. 117, pp. 2675-2676 (1995).
Zhang et al., J. Org. Chem. vol. 65, pp. 6223-6226 (2000).

*Primary Examiner*—Sikarl A Witherspoon
(74) *Attorney, Agent, or Firm*—George W. Johnston; Patricia S. Rocha-Tramaloni; Kimberly J. Prior

(57) ABSTRACT

The invention relates to the preparation of enantiomerically pure (S)-1,1,1-trifluoro-2-propanol by asymmetric hydrogenation of 1,1,1-trifluoroacetone which process comprises hydrogenating 1,1,1-trifluoroacetone in the presence of a ruthenium phosphine complex catalyst represented by formula $$Ru(E)(E')(L)(A)$$

wherein E, E' are both chloro or E is hydrogen and E' is $BH_4$;
L is a chiral diphosphine ligand; and
A is an optionally chiral diamine
wherein hydrogenation occurs in the presence of a weak base, with or without an additive, when E and E' are both chloro or
b) in the absence of a base and an additive when E and E' are hydrogen and $BH_4$.

28 Claims, No Drawings

ASYMMETRIC HYDROGENATION OF 1,1,1-TRIFLUOROACETONE

PRIORITY TO RELATED APPLICATION(S)

This application claims the benefit of European Patent Application No. 06117928.9, filed Jul. 27, 2006, which is hereby incorporated by reference in its entirety.

BACKGROUND OF THE INVENTION

For the preparation of APIs it is absolutely necessary to use isomerically pure building blocks and/or highly stereoselective procedures because by-products in APIs may have adverse effects in the treatment of illnesses. Therefore, a high purity is requested for all APIs.

Enantiomerically pure (S)-1,1,1,-trifluoro-2-propanol is an important building block for the preparation of isomerically pure active pharmaceutical ingredients (APIs), used for the treatment of neurological and neuropsychiatric disorders.

As neither the enantiomeric purity of the building block (S)-1,1,1-trifluoro-2-propanol nor that of its subsequent intermediates in the syntheses of the respective APIs can be enriched, e.g. by crystallization, it is paramount to use (S)-1,1,1-trifluoro-2-propanol of high enantiomerical purity in the synthesis of such APIs.

J. W. C. Crawford (*J. Chem. Soc.* 1967, 2332) described a method for producing (S)-1,1,1-trifluoro-2-propanol, where (rac)-1-(trifluoromethylethoxy)propionic acid (the adduct of the alcohol and acrylic acid) was separated into its optical isomers through its quinine salt, and pure (S)-1,1,1-trifluoro-2-propanol was obtained from the enantiomeric pure alkoxy-acid by alkaline hydrolysis and distillation. Although this method affords (S)-1,1,1-trifluoro-2-propanol of high enantiomeric purity (optical rotation: −5.6°), the method is not suitable for large scale production.

T. C. Rosen et al. (*Chimica Oggi Suppl.* 2004, 43) prepared both (R)- and (S)-1,1,1-trifluoro-2-propanol by asymmetric reduction of 1,1,1-trifluoroacetone using alcohol dehydrogenases (ADHs) either in their natural hosts or as recombinant enzymes expressed in *E. coli*. Resting whole cells or crude cell free extracts may be used and in the latter case addition of a cofactor regenerating system is necessary.

M. Buccierelli et al. (*Synthesis* 1983, 11, 897) describe the preparation of (S)-1,1,1-trifluoro-2-propanol by reduction of 1,1,1-trifluoroacetone using (resting) Baker's yeast on lab scale. Although the reaction proceeds fast (4 h), a 300 times excess of yeast with respect to substrate is required, the substrate concentration is only 2.5 g/kg yeast suspension, and (S)-1,1,1-trifluoro-2-propanol is obtained only with approx. 80% ee (as calculated from the optical rotation of −4.5° for the isolated alcohol, compared with −5.6° for the pure alcohol), a value which is far too low for our needs. In addition, the isolation protocol, based on repeated solvent extraction in combination with distillation, is not applicable economically on large scale.

Asymmetric hydrogenations of trifluoromethyl (aryl or alkyl) ketones using rhodium catalysts of type [Rh((S)-Cy, Cy-oxoProNOP)(OCOCF$_3$)]$_2$ in toluene with up to 98% ee have been reported by A. Kuroki (*Org. Lett.* 2001, 3, 457).

Analogue ruthenium catalysts to types 3 and 4 described herein, but containing BINAP instead of MeOBIPHEP as chiral ligands have been applied in the asymmetric hydrogenation of aryl alkyl ketones (mainly acetophenone and derivatives) with up to 99% ee (R. Noyori et al., *J. Am. Chem. Soc.* 1995, 117, 2675; *Angew. Chem.* 2001, 113, 40; *J. Am. Chem. Soc.* 2002, 124, 6508 and *J. Am. Chem. Soc.* 2003, 125, 13490).

Noyori also reported lately with these Ru-BINAP-catalysts (*J. Am. Chem. Soc.* 2005, 127, 8288) the successful asymmetric hydrogenation of tert.-butyl (alkyl, aryl or alkenyl) ketones. It is reported that catalysts of type 3 always require strong bases (such as alcoholates) as activators (R. Noyori et al., *J. Am. Chem. Soc.* 2003, 125, 13490).

In addition, Noyori described (*J. Am. Chem. Soc.* 2003, 125, 13490) as well that the presence of an alcoholic solvent, such as 2-propanol, ethanol or methanol, is mandatory for optimum reactivity.

SUMMARY OF THE INVENTION

The present invention provides a process for the preparation of chemically and enantiomerically pure (S)-1,1,1-trifluoro-2-propanol by an asymmetric hydrogenation of 1,1,1-trifluoroacetone.

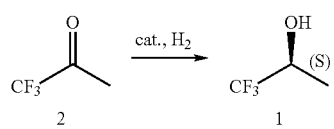

The process of the invention is useful for preparation of (S)-1,1,1-trifluoro-2-propanol with a high enantiomeric excess (ee) and high chemical purity, which may be used as a key building block for the preparation of chemically and enantiomerically pure APIS, for example, as described in WO 2005/014563. The invention also provides a process for preparation of (R)-1,1,1-trifluoro-2-propanol.

The present invention employs ruthenium phosphine complexes of formulas of types 3 and 4. Such complexes have the potential to activate the reaction of compounds of formula 2 to compounds of formula 1 in such a way that the subsequent APIs have the high isomerical purity requested.

Such ruthenium phosphine complexes are represented by the formula

Ru(E)(E')(L)(A)

wherein E and E' are both chloro or E is hydrogen and E' is BH$_4$;

L is a chiral diphosphine ligand; and

A is an optionally chiral diamine.

The ruthenium phosphine complexes of formulas of types 3 and 4 have the structures as follows:

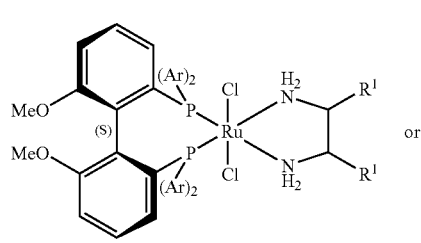

-continued 3-1
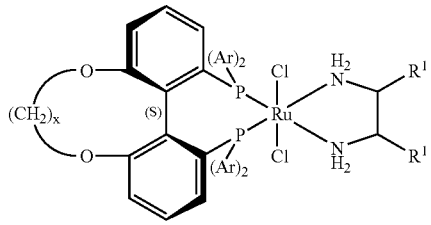

3-2
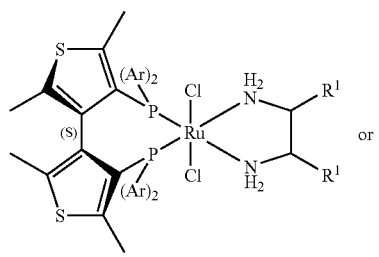
or 3-3
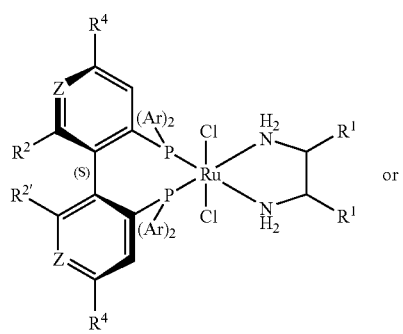
or 3-4
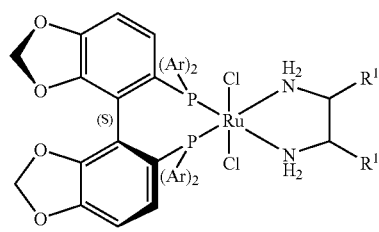

4-1
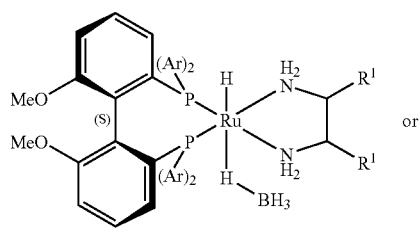
or

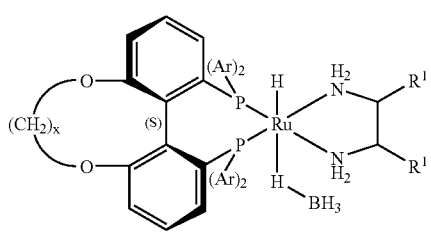

-continued 4-2
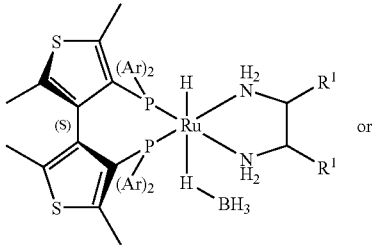
or 4-3
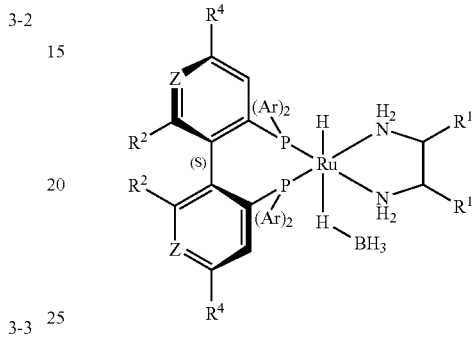

wherein
Ar is phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl group(s);

Z is N or C—$R^3$;

each $R^1$ is independently hydrogen, $C_{1-7}$-alkyl, cycloalkyl or aryl; or taken together form a —$(CH_2)_4$-bridge;

$R^2$ is $C_{1-7}$-alkyl, $C_{1-7}$-alkoxy, hydroxy or —OC(O)—$C_{1-7}$-alkyl;

$R^3$ and $R^4$ are each independently hydrogen, $C_{1-7}$-alkyl, $C_{1-7}$-alkoxy, halogen or di-$C_{1-7}$-alkylamino; or $R^2$ and $R^3$ or $R^3$ and $R^4$ which are attached to the same phenyl group, or both $R^2$ attached to different phenyl groups, taken together, are —X—$(CH_2)_n$—Y—; or —X—$(CF_2)$—X— wherein X is O or C(O)O, Y is O or N($C_{1-7}$-alkyl) and n is an integer from 1 to 6; or $R^2$ and $R^3$ together with the carbon atoms to which they are attached, form a naphthyl or tetrahydronaphthyl ring; and x is an integer from 1 to 6.

It is hereby understood, that if the diamine contains one or two chiral center(s), all possible optical isomers, such as (R,R), (S,S), (rac), (meso), (R) and (S) are comprised.

DETAILED DESCRIPTION OF THE INVENTION

The term "$C_{1-7}$alkyl" denotes a straight-chain or branched saturated hydrocarbon residues with 1-7 carbon atoms, preferably with 1-4 carbon atoms, such as methyl, ethyl, n-propyl, i-propyl and the like.

The term "$C_{1-7}$alkoxy" denotes a $C_{1-7}$alkyl residue as defined above bonded via an oxygen atom.

The term "cycloalkyl" denotes a cyclic saturated hydrocarbon residues with 3-8 carbon atoms, preferably with 3 carbon atoms, such as cyclopropyl.

The term "aryl" denotes an aromatic carbocyclic group consisting of one individual ring, or one or more fused rings in which at least one ring is aromatic in nature. Examples for aryl include phenyl. Examples for substituted aryl include fluorophenyl, difluorophenyl, chlorophenyl, dichlorophenyl, chlorofluorophenyl, cyanophenyl, methylphenyl, methoxyphenyl, fluoromethylphenyl, trifluoromethylphenyl and trifluoromethoxyphenyl.

The "chiral diphosphine ligand" are defined in the catalysts of formulas 3, 3-1, 3-2 and 3-3 and in the table of acronyms of diphosphine ligands on page 19.

The "optionally chiral diamine" are described in paragraph [0031]. They are well known to the skilled person.

The presence of alcoholic solvents and of alcoholates or other strong bases 1,1,1-trifluoroacetone easily undergo aldolization causing the formation of a set of undesired by-products. By using conditions, proposed by Noyori (presence of strong bases and 2-propanol as solvent) no solvent-free pure (S)-1,1,1-trifluoro-2-propanol can be isolated e.g. by simple distillation (cf. comparative experiments 23 and 29). This is especially of importance since alcoholic impurities in (S)-1,1,1-trifluoro-2-propanol such as for example 2-propanol can be incorporated instead of (S)-1,1,1-trifluoro-2-propanol into the API because of their similar reactivity. As a result, the chemical purity of the API is decreased. Furthermore, by using strong bases, but without alcoholic solvents the yield of pure (S)-1,1,1-trifluoro-2-propanol is very low and not suitable for production in large scales.

To overcome such a disadvantage, instead of a strong base, the present invention employs weak organic and inorganic bases, i.e. bases with $pK_b$ values of >7 (relative to water; cf. D. R. Lide "Handbook for Chemistry and Physics", CRC press 1994, section 8-44 to 8-55, such as for example ammonium, transition metal, alkali metal and alkali earth metal salts of $HCOO^-$, $AcO^-$, $CF_3COO^-$, $tBuCOO^-$, $HCO_3^-$ $HSO_4^-$, $SO_4^{2-}$, $HSO_3^-$, $H_2PO_3^-$, $HPO_3^{2-}$ and phenolates such as e.g. 2,4-dinitrophenolate as activators are highly beneficial if applied in combination with a catalyst of type 3. Thereby, the present invention suppresses the undesired aldolization of 1,1,1-trifluoroacetone to yield at very low catalyst loading (S/C 20,000) highly pure (S)-1,1,1-trifluoroisopropanol of >95% ee.

Furthermore, in contradiction to the opinion that the presence of an alcoholic solvent is mandatory for optimum reactivity, the present invention successful demonstrates that the reaction can run more efficiently in the absence of a solvent. In addition, additives such as water or small amounts of 1,1,1-trifluoroisopropanol, which never has been described in the literature, have a beneficial influence on reaction rate and selectivity.

In addition, catalysts of type 4 are active in the absence of a base and in absence of an additive. Therefore this type of catalyst would be perfect for the asymmetric hydrogenation of highly base sensitive substrates such as 1,1,1-trifluoroacetone. However, an additional technically synthetic step is necessary to prepare 4 from 3.

The asymmetric hydrogenation is carried out in the presence of a ruthenium phosphine complex represented by the formula Ru(E)(E')(L)(A)

wherein E and E' are both chloro or E is hydrogen and E' is $BH_4$;
L is a chiral diphosphine ligand; and
A is an optionally chiral diamine.

Asymmetric Hydrogenation of 1,1,1-trifluoroacetone with Catalysts 3 (E=E'=Cl)

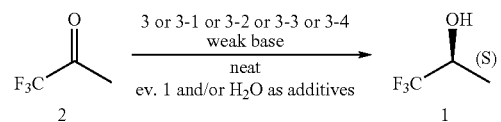

wherein the catalysts are

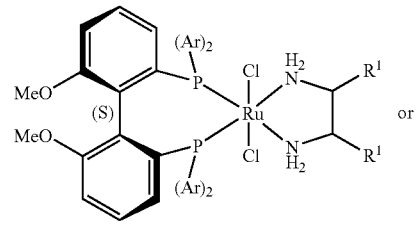

3

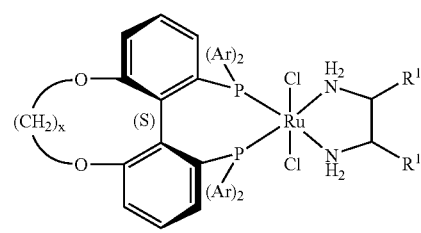

3-1

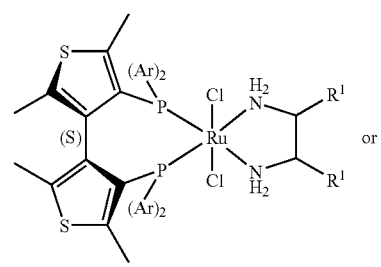

3-2

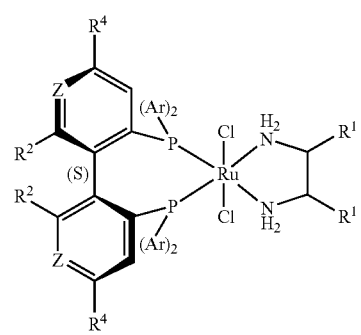

3-3

-continued 3-4

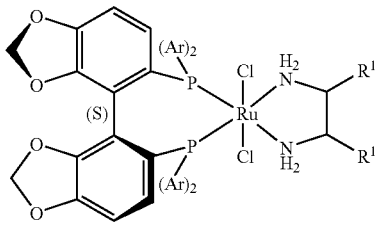

wherein
Ar is phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl group(s);

Z is N or C—$R^3$;

each $R^1$ is independently hydrogen, $C_{1-7}$-alkyl, cycloalkyl or aryl; or taken together form a —$(CH_2)_4$-bridge;

$R^2$ is $C_{1-7}$-alkyl, $C_{1-7}$-alkoxy, hydroxy or —OC(O)—$C_{1-7}$-alkyl;

$R^3$ and $R^4$ are each independently hydrogen, $C_{1-7}$-alkyl, $C_{1-7}$-alkoxy, halogen or di-$C_{1-7}$-alkylamino; or $R^2$ and $R^3$ or $R^3$ and $R^4$ which are attached to the same phenyl group, or both $R^2$ attached to different phenyl groups, taken together, are —X—$(CH_2)_n$—Y—; or —X—$(CF_2)$—X— wherein X is O or C(O)O, Y is O or N($C_{1-7}$-alkyl) and n is an integer from 1 to 6; or $R^2$ and $R^3$ together with the carbon atoms to which they are attached, form a naphthyl or tetrahydronaphthyl ring; and x is an integer from 1 to 6.

It is hereby understood, that if the diamine contains one or two chiral center(s), all possible optical isomers, such as (R,R), (S,S), (rac), (meso), (R) and (S) are comprised.

The corresponding diphosphine ligands are known in the art and are commercially available, or can be prepared for example as described in EP 0398 132 and WO 92/16535 (MeOBIPHEP, 3,5-iPr-MEOBIPHEP), in EP 104375 (BI-PHEMP) and in EP 580 331 (BINAP).

The optionally chiral diamines are for example compounds of formulae

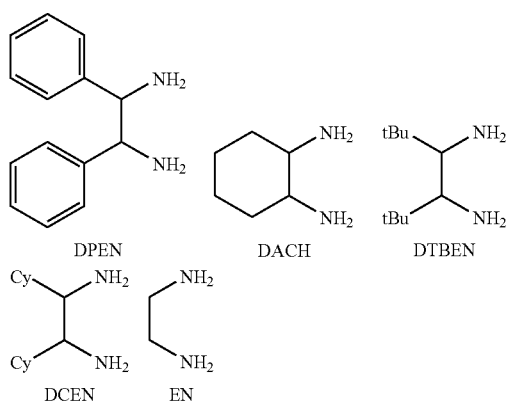

wherein tBu signifies tert.-butyl, Me is methyl and Cy stands for cyclohexyl.

The diamines are commercially available or can be prepared according to known methods.

The preferred catalysts are

3

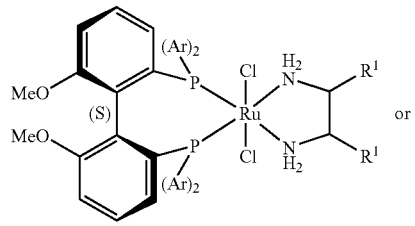

or 3-1

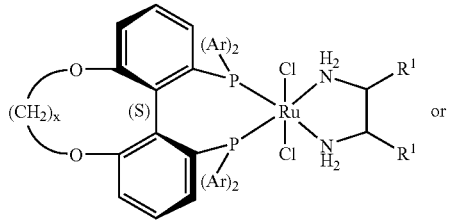

or 3-4

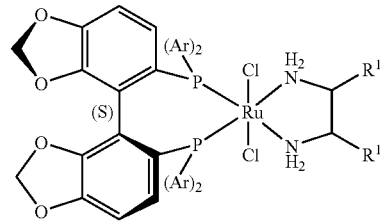

wherein
Ar is

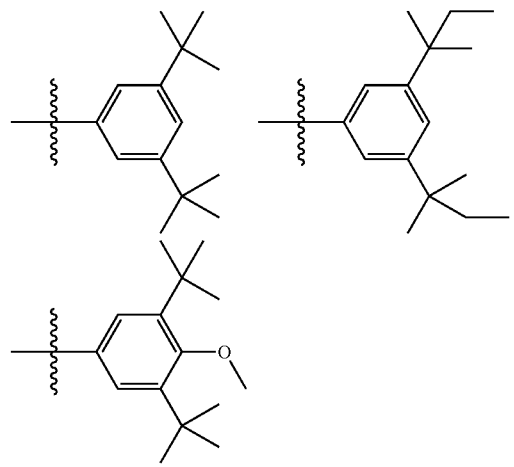

$R^1$ is phenyl; and
x is 2 or 3.

It is hereby understood, that all possible optical isomers of the diamine, such as (R,R), (S,S), (rac) and (meso) are comprised.

A catalyst of type 3 can be prepared, isolated and characterized in analogy to the methods described in *Angew. Chem. Int. Ed.* 1998, 37, 1703, or can be prepared in accordance with examples 30-40, for example, as follows:

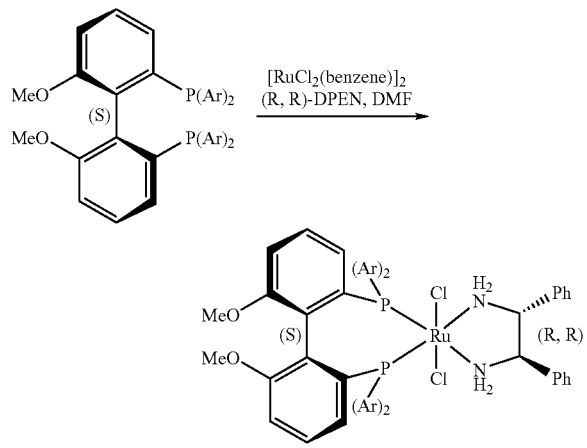

wherein Ar is as described above.

A preferred catalyst is [RuCl₂((S)-3,5-tBu-MeOBIPHEP)((R,R)-DPEN)], which can be prepared as follows:

In analogy to R. Noyori et al. (*J. Am. Chem. Soc.* 1995, 117, 2675), a 2-necked round-bottomed flask equipped with a reflux condenser is charged under an argon atmosphere with (S)-3,5-tBu-MeOBIPHEP, [RuCl₂(benzene)]₂ and DMF. The solution is stirred at 100° C. for 10 min. At r.t., (R,R)-DPEN is added, and the solution is stirred at r.t. for 6 days. The volatiles are removed by rotatory evaporation (10³ Pa, 60° C.), and the residue is dried under vacuum (100 Pa) at r.t. for 2 h. Hexane is added to the residue, and the formed suspension is stirred at r.t. for 10 min. The supernatant is removed by suction with a micro-filter candle and the filtrate is rotatory evaporated to dryness.

The asymmetric hydrogenation with catalysts of type 3 is carried out in the presence of weak bases, such as ammonium, transition metal, alkali metal and alkali earth metal salts of HCOO⁻, AcO⁻, CF₃COO⁻, tBuCOO⁻, HCO₃⁻ HSO₄⁻, SO₄²⁻, HSO₃⁻, H₂PO₃⁻, HPO₃²⁻ and phenolates such as e.g. 2,4-dinitrophenolate.

General Description of the Asymmetric Hydrogenation with Catalysts of Type 3

A stainless steel autoclave is charged on air with 1,1,1-trifluoroacetone and with a catalyst of type 3, 3-1, 3-2, 3-3 or 3-4, such as [RuCl₂((S)-3,5-tBu-MeOBIPHEP)((R,R)-DPEN)] (S/C 12,500), a weak base (0.01-10 mol-% relative to 2), such as sodium formate and an additive (0.1-50 wt-% relative to 2), such as water or (S)-1,1,1-trifluoro-2-propanol. The autoclave is sealed, and the hydrogenation is run under stirring at a temperature between about 20-80° C., preferably between about 40 and 60° C., and at a pressure between about 5×10⁵–100×10⁵ Pa, preferably between about 40×10⁵ and 80×10⁵ Pa of hydrogen. After about 20 h the autoclave is vented and opened. Crude product incl. additive is isolated. Bulb-to-bulb distillation of the crude product (oven temperature: r.t. to 130° C., 1 atm) afforded (S)-1,1,1-trifluoro-2-propanol.

The substrate-to-catalyst molar ratio (S/C) is 1,000-100,000, preferably 10,000-30,000.

A preferred variant for the preparation of enantiomerically pure (S)-1,1,1-trifluoro-2-propanol comprises hydrogenating 1,1,1-trifluoroacetone in the presence of a ruthenium phosphine complex represented by formula

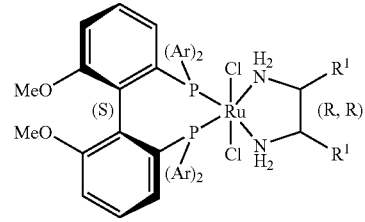

wherein
Ar is

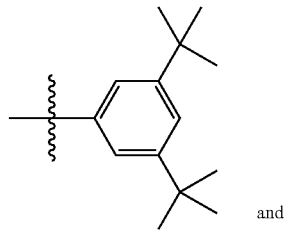
and

R¹ is phenyl in the presence of 0.04-0.5 mol-% (relative to 2) of HCOONa and 1-3 wt-% (relative to 2) of water, by a substrate-to-catalyst molar ratio (S/C) of 10,000-30,000, at 40-60° C. and 40×10⁵–80×10⁵ Pa of hydrogen.

Examples for Hydrogenation with Catalyst of Type 3:

| Expl | catalyst | Ar | R¹ | diamin config. | additive | base | % ee | % purity | % yield |
|---|---|---|---|---|---|---|---|---|---|
| 1 | 3 | 3,5-di-tBu-phenyl | phenyl | (R,R) | H₂O | HCOONa | 99.2 | >99.9 | 86 |

-continued

| Expl | catalyst | Ar | R¹ | diamin config. | additive | base | % ee | % purity | % yield |
|---|---|---|---|---|---|---|---|---|---|
| 1.2 | 3 | 3,5-di-t-Bu-phenyl | phenyl | (R,R) | H₂O | HCOONa | 99.2 | 99.6 | 96 |
| 2 | 3-1 x = 3 | 3,5-di-t-Bu-phenyl | phenyl | (R,R) | H₂O | HCOONa | 99.3 | >99.9 | 81 |
| 3 | 3 | 3,5-di-t-Bu-phenyl | phenyl | (R,R) | 1 | HCOONa | 99.0 | 98.2 | 77 |
| 4 | 3 | 3,5-di-t-Bu-phenyl | phenyl | (R,R) | no | HCOONa | 97.0 | 99.1 | 88 |
| 5 | 3 | 3,5-di-t-Bu-phenyl | phenyl | (R,R) | 1 | NaOC(Me)(CF₃) | 98.9 | 90.2 | 31 |
| 6 | 3 | 3,5-di-t-Bu-phenyl | phenyl | (R,R) | no | Et₃N | 99.0 | 70.5 | 35 |

-continued

| Expl | catalyst | Ar | R¹ | diamin config. | additive | base | % ee | % purity | % yield |
|---|---|---|---|---|---|---|---|---|---|
| 7 | 3 | 3,5-di-tert-butylphenyl | phenyl | (R,R) | no | KOtBu | 95.8 | 90.4 | 19 |
| 8 | 3 | 3,5-di-tert-butylphenyl | phenyl | (R,R) | no | NaOAc | 97.0 | 97.3 | 40 |
| 9 | 3 | 3,5-di-tert-butylphenyl | phenyl | (R,R) | no | HCOONa | 97.9 | 97.3 | 50 |
| 10 | 3 | 3,5-di-tert-butylphenyl | phenyl | (R,R) | no | NaHCO₃ | 96.5 | 96.6 | 66 |
| 11 | 3 | 3,5-di-tert-butylphenyl | phenyl | (R,R) | no | CsCO₃ | 97.7 | 89.7 | 21 |
| 12 | 3 | 3,5-di-tert-butylphenyl | phenyl | (R,R) | no | NaOPh | 94.8 | 86.5 | 11 |

-continued

| Expl | catalyst | Ar | R¹ | diamin config. | additive | base | % ee | % purity | % yield |
|---|---|---|---|---|---|---|---|---|---|
| 13 | 3 | 3,5-di-tert-butylphenyl | phenyl | (R,R) | no | AgOAc | 95.7 | 98.3 | 58 |
| 14 | 3 | 3,5-diisopropylphenyl | phenyl | (R,R) | 1 | HCOONa | 97.6 | 82.2 | 40 |
| 15 | 3 | 3,5-di-tert-amylphenyl | phenyl | (R,R) | 1 | HCOONa | 98.7 | 96.4 | 78 |
| 16 | 3 | 3,5-di-tert-butyl-4-methoxyphenyl | phenyl | (R,R) | 1 | HCOONa | 98.0 | 93.2 | 76 |
| 16.2 | 3-4 | 3,5-di-tert-butyl-4-methoxyphenyl | phenyl | (R,R) | H₂O | HCOONa | 98.8 | 98.9 | 88 |
| 17 | 3 | 3,5-di-tert-butylphenyl | H | — | H₂O | HCOONa | 95.9 | 97.7 | 33 |

-continued
| Expl | catalyst | Ar | R¹ | diamin config. | additive | base | % ee | % purity | % yield |
|---|---|---|---|---|---|---|---|---|---|
| 18 | 3 | 3,5-dimethylphenyl | phenyl | (R,R) | no | AgOAc | 95.8 | 95.1 | 47 |
| 19 | 3 | 3,5-di-tert-butylphenyl | phenyl | (rac) | H₂O | HCOONa | 98.7 | >99.9 | 98 |
| 20 | 3 | 3,5-di-tert-butylphenyl | phenyl | (R,R) | H₂O | HCOONa | 99.2 | 99.8 | 95 |
| 21 | 3 | phenyl | phenyl | (R,R) | H₂O | HCOONa | 98.0 | 74.8 | 40 |
| 22 | 3-2 | phenyl | phenyl | (R,R) | H₂O | HCOONa | 93.2 | 67.1 | 32 |
Asymmetric Hydrogenation of 1,1,1-trifluoroaceton with Catalysts 4 (E=H and E'=BH₄
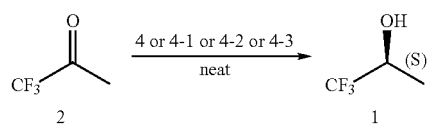
wherein the catalysts are
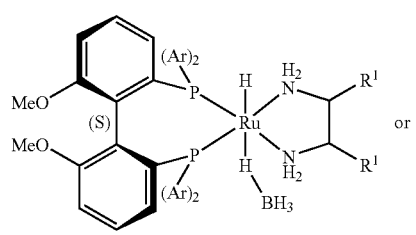
4
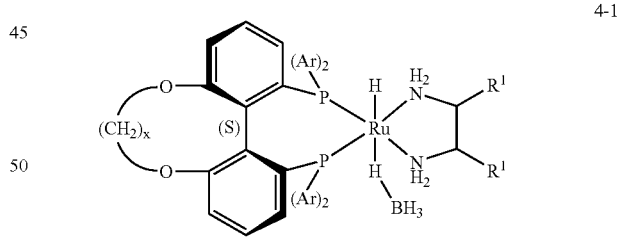
4-1
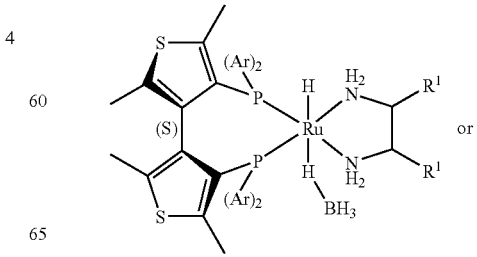
4-2 or -continued

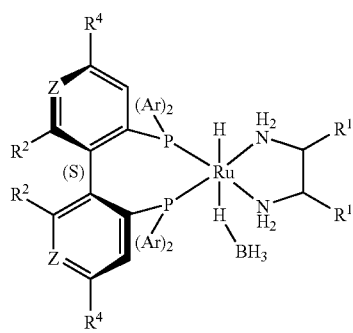
4-3 wherein
Ar is phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl group(s);
Z is N or C—$R^3$;
each $R^1$ is independently hydrogen, $C_{1-7}$-alkyl, cycloalkyl or aryl; taken together form a —$(CH_2)_{4-}$ bridge;
$R^2$ is $C_{1-7}$-alkyl, $C_{1-7}$-alkoxy, hydroxy or —OC(O)—$C_{1-7}$-alkyl;
$R^3$ and $R^4$ are each independently hydrogen, $C_{1-7}$-alkyl, $C_{1-7}$-alkoxy, halogen or di-$C_{1-7}$-alkylamino; or
$R^2$ and $R^3$ or $R^3$ and $R^4$ which are attached to the same phenyl group, or both $R^2$ attached to different phenyl groups, taken together, are —X—$(CH_2)_n$—Y—; or —X—$(CF_2)$—X— wherein X is O or C(O)O, Y is O or N($C_{1-7}$-alkyl) and n is an integer from 1 to 6; or
$R^2$ and $R^3$ together with the carbon atoms to which they are attached, form a naphthyl or tetrahydronaphthyl ring; and
x is an integer from 1 to 6.

It is hereby understood, that if the diamine contains one or two chiral center(s), all possible optical isomers, such as (R,R), (S,S), (rac), (meso), (R) and (S) are comprised.

Above-mentioned diphosphine ligands are known in the art and are commercially available or can be prepared for example as described in EP 0398 132 and WO 92/16535 (MeOBIPHEP, 3,5-iPr-MEOBIPHEP), in EP 104375 (BIPHEMP) and in EP 580 331 (BINAP).

The optionally chiral diamines are for example compounds of formulae

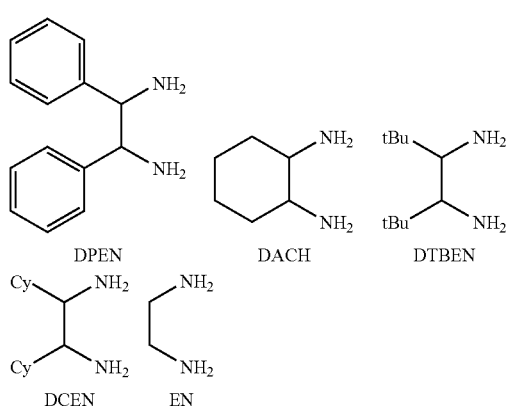

wherein tBu signifies tert.-butyl, Me is methyl and Cy stands for cyclohexyl.

The diamines are commercially available or can be prepared according to known methods.

The preferred catalysts are

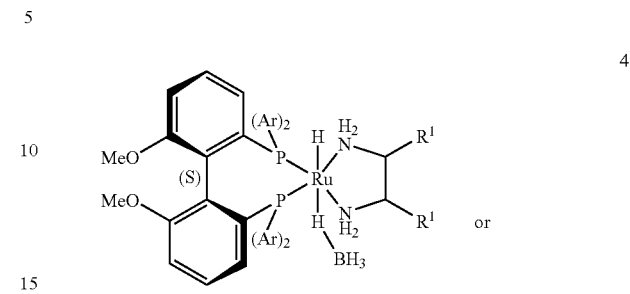
4

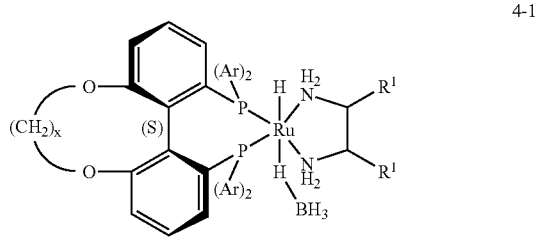
4-1 wherein
Ar is

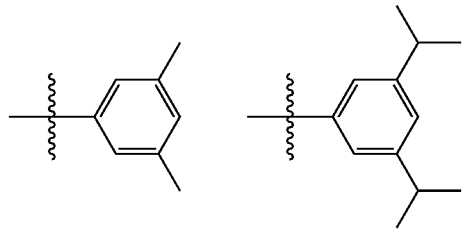

$R^1$ is phenyl; and
x is 2 or 3.

It is hereby understood, that all possible optical isomers of the diamine, such as (R,R), (S,S), (rac) and (meso) are comprised;

A catalyst of type 4 can be prepared, isolated and characterized in analogy to the methods described in *Angew. Chem., Int. Ed.* 1998, 37, 1703, or can be prepared in accordance with examples 41-45, for example, as follows:

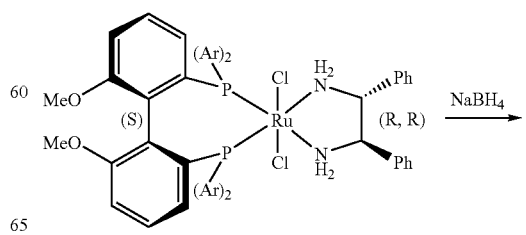
3

-continued

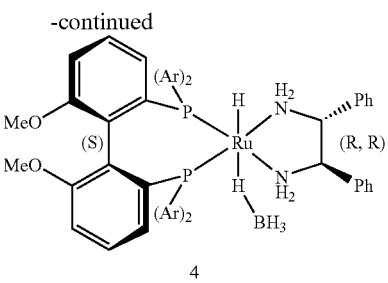

4 wherein
Ar is as described above

A preferred catalyst is [RuH(BH₄)((S)-MeOBIPHEP)((R,R)-DPEN)], which may be prepared as follows:

In analogy to R. Noyori et al. (*J. Am. Chem. Soc.* 2002, 124, 6508), a 2-necked round-bottomed flask equipped with a reflux condenser is charged under an argon atmosphere with [RuCl₂((S)-MeOBIPHEP)((R,R)-DPEN)], sodium borohydride, toluene and ethanol. The solution is stirred at 65° C. for 10 min and at r.t. for 30 min. The suspension is concentrated to a volume of ca. 20 ml by rotatory evaporation (2×10³ Pa, 40° C.). Toluene is added, and the suspension is filtered through a Celite pad. The filtrate is evaporated to dryness (2×10³ Pa, 40° C.).

General Description of the Asymmetric Hydrogenation with Catalysts of Type 4

A stainless steel autoclave is charged on air with 1,1,1-trifluoroacetone and with a catalyst of type 4, 4-1, 4-2 or 4-3, for example with [RuH(BH₄)((S)-MeOBIPHEP)((R,R)-DPEN)] (S/C 2,000). The autoclave is sealed, and the hydrogenation runs under stirring at temperatures between 20-80° C., preferably between 40 and 60° C. and at a pressure of 5×10⁵–100×10⁵ Pa, preferably between 40×10⁵ and 80×10⁵ Pa of hydrogen. After about 24 h the autoclave is vented and opened. Crude product is isolated. Bulb-to-bulb distillation of the crude product afforded (S)-1,1,1-trifluoro-2-propanol.

The substrate-to-catalyst molar ratio (S/C) is 1,000-50,000, preferably 2,000-20,000. A preferred variant for preparation of enantiomerically pure (S)-1,1,1-trifluoro-2-propanol comprises hydrogenating 1,1,1-trifluoroacetone in the presence of a ruthenium phosphine complex represented by formula

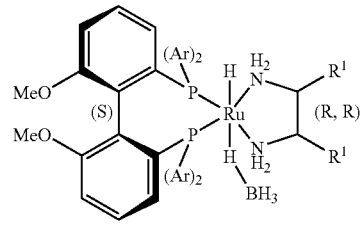

4 wherein
Ar is

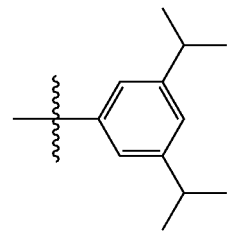

and $R^1$ is phenyl without a base or additive by a substrate-to-catalyst molar ratio (S/C) of 2,000-20,000, between 40 and 60° C. and between 40×10⁵ and 80×10⁵ Pa of hydrogen.

Examples for Hydrogenation with Catalyst of Type 4

| Expl | catalyst | Ar | $R^1$ | diamin config. | % ee | % purity | % yield |
|---|---|---|---|---|---|---|---|
| 24 | 4 | phenyl | phenyl | (R,R) | 94.2 | >99.9 | 53 |
| 25 | 4 | 3,5-dimethylphenyl | phenyl | (R,R) | 92.4 | 98.9 | 75 |
| 26 | 4 | 3,5-dimethylphenyl | phenyl | (S,S) | 89.2 | >99.9 | 76 |

-continued

| Expl | catalyst | Ar | R¹ | diamin config. | % ee | % purity | % yield |
|---|---|---|---|---|---|---|---|
| 27 | 4 | 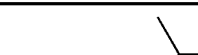 | phenyl | (R,R) | 97.4 | >99.9 | 55 |
| 28 | 4-2 | 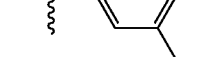 | phenyl | (R,R) | 93.3 | 92.7 | 42 |

Abbreviations

DPEN=1,2-diphenylethylene-1,2-diamine;
EN=ethylendiamine; r.t.=room temperature;
DMF=dimethylformamide.
Acronyms of diphosphine ligands:

| | |
|---|---|
| MeOBIPHEP | Phosphine, [6,6'-dimethoxy[1,1'-biphenyl]-2,2'-diyl]bis[diphenyl]- |
| TMBTP | 2,2',5,5'-Tetramethyl-4,4'-bis(diphenylphosphino)-3,3'-bithiophene |
| 3,5-Xyl-MeOBIPHEP | Phosphine, [6,6'-dimethoxy[1,1'-biphenyl]-2,2'-diyl]bis[bis(3,5-dimethylphenyl)- |
| 3,5-tBu-MeOBIPHEP | Phosphine, (6,6'-dimethoxy[1,1'-biphenyl]-2,2'-diyl)bis[bis(3,5-di-tert.-butyl-phenyl)- |
| 3,5-tPe-MeOBIPHEP | Phosphine, (6,6'-dimethoxy[1,1'-biphenyl]-2,2'-diyl)bis[bis(3,5-di-tert.-pentyl-phenyl)- |
| 3,5-iPr-MeOBIPHEP | Phosphine, (6,6'-dimethoxy[1,1'-biphenyl]-2,2'-diyl)bis[bis(3,5-di-isopropyl-phenyl)- |
| 3,5-tBu-4-MeO-MeOBIPHEP | Phosphine, (6,6'-dimethoxy[1,1'-biphenyl]-2,2'-diyl)bis[bis(3,5-di-tert.-butyl-4-methoxy-phenyl)- |
| 3,5-tBu-C3-Tuna-MeOBIPHEP | Phosphine, (6,6'-propylene-oxy[1,1'-biphenyl]-2,2'-diyl)bis[bis(3,5-di-tert.-pentyl-phenyl)- |
| DTBM-SEGPHOS | Phosphine, 1,1'-[[4,4'-bi-1,3-benzodioxole]-5,5'-diyl]bis[1,1-bis[3,5-bis(1,1-dimethylethyl)-4-methoxyphenyl]- |

| catalyst structure (synthesized) | chemical name |
|---|---|
| 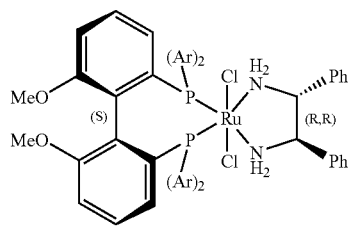 | [RuCl₂((S)-3,5-tBu-MeOBIPHEP)((R,R)-DPEN)] |
| Ar = 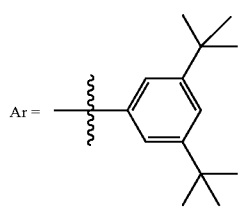 | |

-continued

| catalyst structure (synthesized) | chemical name |
|---|---|
| | [RuCl$_2$((S)-3,5-tBu-C3-Tuna-MeOBIPHEP)((R,R)-DPEN)] |
| Ar = 3,5-di-tert-butylphenyl | |
| | [RuCl$_2$((S)-MeOBIPHEP)((R,R)-DPEN)] |
| | [RuCl$_2$((S)-3,5-Xyl-MeOBIPHEP)((R,R)-DPEN)] |
| Ar = 3,5-dimethylphenyl | |
| | [RuCl$_2$((S)-3,5-Xyl-MeOBIPHEP)((S,S)-DPEN)] |
| Ar = 3,5-dimethylphenyl | |

-continued

| catalyst structure (synthesized) | chemical name |
|---|---|
| (structure) Ar = 3,5-diisopropylphenyl | [RuCl₂((S)-3,5-iPr-MeOBIPHEP)((R,R)-DPEN)] |
| (structure) Ar = 3,5-di-tert-pentylphenyl | [RuCl₂((S)-3,5-tPe-MeOBIPHEP)((R,R)-DPEN)] |
| (structure) Ar = 3,5-di-tert-butyl-4-methoxyphenyl | [RuCl₂((S)-3,5-tBu-4-MeO-MeOBIPHEP)((R,R)-DPEN)] |

-continued

| catalyst structure (synthesized) | chemical name |
|---|---|
| (structure) | [RuCl₂((S)-TMBTP)((R,R)-DPEN)] |
| (structure) | [RuCl₂((S)-3,5-tBu-MeOBIPHEP)(EN)] |
| (structure) | [RuCl₂((S)-3,5-tBu-MeOBIPHEP)((rac)-DPEN)] |
| (structure) | [RuCl₂((S)-DTBM-SEGPHOS)((R,R)-DPEN)] |

-continued

| catalyst structure (synthesized) | chemical name |
|---|---|
| | [RuH(BH$_4$)((S)-MeOBIPHEP)((R,R)-DPEN)] |
| | [RuH(BH$_4$)((S)-3,5-Xyl-MeOBIPHEP)((R,R)-DPEN)] |
| Ar = 3,5-dimethylphenyl | |
| | [RuH(BH$_4$)((S)-3,5-Xyl-MeOBIPHEP)((S,S)-DPEN)] |
| Ar = 3,5-dimethylphenyl | |
| | [RuH(BH$_4$)((S)-3,5-iPr-MeOBIPHEP)((R,R)-DPEN)] |
| Ar = 3,5-diisopropylphenyl | |

| catalyst structure (synthesized) | chemical name |
|---|---|
| (structure diagram) | [RuH(BH₄)((S)-TMBTP)((R,R)-DPEN)] |

Asymmetric Hydrogenation of 1,1,1-Trifluoroacetone using Ruthenium-Dichloro-Catalysts

EXAMPLES 1-22

Example 1

(S)-1,1,1-Trifluoro-2-propanol

A 35-ml stainless steel autoclave was charged on air with 3.125 g of 1,1,1-trifluoroacetone (27.89 mmol), 3.16 mg of [RuCl$_2$((S)-3,5-tBu-MeOBIPHEP)((R,R)-DPEN)] ($2.23 \times 10^{-6}$ mol, S/C 12,500), 0.80 mg of sodium formate ($11.5 \times 10^{-6}$ mol) and 0.100 g of water as additive. The autoclave was sealed and the hydrogenation was run under stirring at 40° C. and $40 \times 10^5$ Pa of hydrogen. After 20 h the autoclave was vented and opened. Crude product (2.970 g, incl. additive) with 99.2% ee and >99.9% purity was isolated as a yellowish oil. Bulb-to-bulb distillation of the crude product (oven temperature: r.t. to 130° C., 1 atm) afforded 86% (corrected) of the title compound (2.836 g, incl. additive) as a colorless oil with 99.2% ee and >99.9% purity.

$^1$H NMR (300 MHz, CDCl$_3$): 4.12 (qd, 1H, J=6.2, 6.1 Hz); 2.05 (d, 1H, J=6.1 Hz); 1.38 (d, 3H, J=6.2 Hz). GC method for the determination of purity and ee: Column: BGB-174 (30 m, I.D. 0.25 mm); oven: 60° C. (5 min) to 160° C. (3° C./min); injector: 180° C.; detector: 200° C.; carrier gas: H$_2$ (90 kPa); split ratio: 1/40. Sample preparation: 2-4 mg of the sample were dissolved in 0.5 ml ethyl acetate; 1 μl was injected. Retention times: 13.0 min, (R)-1,1,1-trifluoro-2-propanol; 13.5 min, (S)-1,1,1-trifluoro-2-propanol.

Example 1.2

(S)-1,1,1-Trifluoro-2-propanol

In analogy to Example 1, a 185-ml stainless steel autoclave was charged in the glove box with 0.75 ml of water (additive), 14.86 mg of [RuCl$_2$((S)-3,5-tBu-MeOBIPHEP)((R,R)-DPEN)] ($10.5 \times 10^{-6}$ mol, S/C 20,000), 75.00 mg of sodium formate (1.10 mmol) and 23.44 g of 1,1,1-trifluoroacetone (209.2 mmol). The autoclave was sealed and the hydrogenation was run under stirring at 40° C. and $40 \times 10^5$ Pa of hydrogen. After 10 h the reaction temperature was increased for 2 h to 60° C. Then the autoclave was vented and opened. Crude product (24.55 g, incl. additive) with 99.2% ee and 99.1% purity was isolated. Distillation of the crude product at 34° C./150 mbar afforded 96% (corrected) of the title compound (23.91 g, incl. additive) as a colorless oil with 99.2% ee and 99.6% purity.

Example 2

(S)-1,1,1-Trifluoro-2-propanol

A 35-ml stainless steel autoclave was charged on air with 3.125 g of 1,1,1-trifluoroacetone (27.89 mmol), 1.99 mg of [RuCl$_2$((S)-3,5-tBu-C3-Tuna-MeOBIPHEP)((R,R)-DPEN)] ($1.39 \times 10^{-6}$ mol, S/C 20,000), 0.80 mg of sodium formate ($11.5 \times 10^{-6}$ mol) and 0.100 g of water as additive. The autoclave was sealed and the hydrogenation was run under stirring at 40° C. and $40 \times 10^5$ Pa of hydrogen. After 20 h the autoclave was vented and opened. Crude product (2.825 g, incl. additive) with 99.3% ee and >99.9% purity was isolated as a yellowish oil. Bulb-to-bulb distillation of the crude product (oven temperature: r.t. to 130° C., 1 atm) afforded 81% (corrected) of the title compound (2.665 g, incl. additive) as a colorless oil with 99.3% ee and >99.9% purity.

Example 3

(S)-1,1,1-Trifluoro-2-propanol

A 35-ml stainless steel autoclave was charged on air with 3.125 g of 1,1,1-trifluoroacetone (27.89 mmol), 3.16 mg of [RuCl$_2$((S)-3,5-tBu-MeOBIPHEP)((R,R)-DPEN)] ($2.23 \times 10^{-6}$ mol, S/C 12,500), 0.80 mg of sodium formate ($11.5 \times 10^{-6}$ mol) and 0.102 g of (S)-1,1,1-trifluoro-2-propanol (0.89 mmol, 99.3% ee) as additive. The autoclave was sealed and the hydrogenation was run under stirring at 40° C. and $40 \times 10^5$ Pa of hydrogen. After 20 h the autoclave was vented and opened. Crude product (2.974 g, incl. additive) with 99.0% ee and 88.8% purity was isolated as a yellowish oil. Bulb-to-bulb distillation of the crude product (oven temperature: r.t. to 130° C., 1 atm) afforded 77% (corrected) of the title compound (2.606 g, incl. additive) as a colorless oil with 99.0% ee and 98.2% purity.

Example 4

(S)-1,1,1-Trifluoro-2-propanol

A 35-ml stainless steel autoclave was charged on air with 3.125 g of 1,1,1-trifluoroacetone (27.89 mmol), 1.97 mg of [RuCl$_2$((S)-3,5-tBu-MeOBIPHEP)((R,R)-DPEN)] ($1.39 \times 10^6$ mol, S/C 12,500) and 0.80 mg of sodium formate ($11.5 \times 10^{-6}$ mol). The autoclave was sealed and the hydrogenation was run under stirring at 40° C. and $40 \times 10^5$ Pa of hydrogen. After 64 h the autoclave was vented and opened. Crude product (2.911 g) with 97.4% ee and 98% purity was isolated as a yellowish oil. Bulb-to-bulb distillation of the crude product (oven temperature: r.t. to 130° C., 1 atm)

afforded 88% of the title compound (2.814 g) as a colorless oil with 97.0% ee and 99.1% purity.

Example 5

(S)-1,1,1-Trifluoro-2-propanol

A 35-ml stainless steel autoclave was charged on air with 3.125 g of 1,1,1-trifluoroacetone (27.89 mmol), 4.00 mg of [RuCl$_2$((S)-3,5-tBu-MeOBIPHEP)((R,R)-DPEN)] (2.82×10$^{-6}$ mol, S/C 10,000), 1.50 mg of sodium (rac)-1,1,1-trifluoro-2-propanolate (11.5×10$^{-6}$ mol) and 1.035 g of (S)-1,1,1-trifluoro-2-propanol (9.06 mmol, 99.3% ee) as additive. The autoclave was sealed and the hydrogenation was run under stirring at 40° C. and 40×10$^5$ Pa of hydrogen. After 20 h the autoclave was vented and opened. Crude product (2.770 g, incl. additive) with 99.0% ee and 75.1% purity was isolated as a yellowish oil. Bulb-to-bulb distillation of the crude product (oven temperature: r.t. to 130° C., 1 atm) afforded 31% of the title compound (2.128 g, incl. additive) as a colorless oil with 98.9% ee and 90.2% purity.

Example 6

(S)-1,1,1-Trifluoro-2-propanol

A 35-ml stainless steel autoclave was charged on air with 3.125 g of 1,1,1-trifluoroacetone (27.89 mmol), 16.00 mg of [RuCl$_2$((S)-3,5-tBu-MeOBIPHEP)((R,R)-DPEN)] (11.30×10$^{-6}$ mol, S/C 2,500) and 1.56 µl of triethylamine (11.2×10$^{-6}$ mol). The autoclave was sealed and the hydrogenation was run under stirring at 40° C. and 40×10$^5$ Pa of hydrogen. After 24 h the autoclave was vented and opened. Crude product (1.659 g) with 99.0% ee and 70.5% purity was isolated as a yellowish oil. Bulb-to-bulb distillation of the crude product (oven temperature: r.t. to 130° C., 1 atm) afforded 35% of the title compound (1.166 g) as a colorless oil with 98.8% ee and 94.4% purity.

Example 7

(S)-1,1,1-Trifluoro-2-propanol

In an analogous manner to Example 6 but in the presence of 1.30 mg potassium tert.-butylat (11.5×10$^{-6}$ mol) instead of triethylamine as base, the tile compound was isolated after bulb-to-bulb distillation in 19% yield (0.681 g) with 95.8% ee and 90.4% purity.

Example 8

(S)-1,1,1-Trifluoro-2-propanol

In an analogous manner to Example 6 but in the presence of 1.00 mg sodium acetate (11.5×10$^{-6}$ mol) instead of triethylamine as base, the tile compound was isolated after bulb-to-bulb distillation in 40% yield (1.320 g) with 97.0% ee and 97.3% purity.

Example 9

(S)-1,1,1-Trifluoro-2-propanol

In an analogous manner to Example 6 but in the presence of 0.80 mg sodium formate (11.5×10$^{-6}$ mol) instead of triethylamine as base, the tile compound was isolated after bulb-to-bulb distillation in 50% yield (1.626 g) with 97.9% ee and 97.3% purity.

Example 10

(S)-1,1,1-Trifluoro-2-propanol

In an analogous manner to Example 6 but in the presence of 1.00 mg sodium hydrogen carbonate (11.5×10$^{-6}$ mol) instead of triethylamine as base, the tile compound was isolated after bulb-to-bulb distillation in 66% yield (0.737 g) with 96.5% ee and 96.6% purity.

Example 11

(S)-1,1,1-Trifluoro-2-propanol

In an analogous manner to Example 6 but in the presence of 3.60 mg cesium carbonate (11.5×10$^{-6}$,mol) instead of triethylamine as base, the tile compound was isolated after bulb-to-bulb distillation in 21% yield (0.737 g) with 97.7% ee and 89.7% purity.

Example 12

(S)-1,1,1-Trifluoro-2-propanol

In an analogous manner to Example 6 but in the presence of 2.00 mg sodium phenolat trihydrate (11.5×10$^{-6}$ mol) instead of triethylamine as base, the tile compound was isolated after bulb-to-bulb distillation in 11% yield (0.407 g) with 94.8% ee and 86.5% purity.

Example 13

(S)-1,1,1-Trifluoro-2-propanol

In an analogous manner to Example 6 but in the presence of 3.80 mg silver(I) acetate (11.5×10$^{-6}$ mol) instead of triethylamine as base, the tile compound was isolated after bulb-to-bulb distillation in 58% yield (1.880 g) with 95.7% ee and 98.3% purity.

Example 14

(S)-1,1,1-Trifluoro-2-propanol

A 35-ml stainless steel autoclave was charged on air with 3.125 g of 1,1,1-trifluoroacetone (27.89 mmol), 2.90 mg of [RuCl$_2$((S)-3,5-iPr-MeOBIPHEP)((R,R)-DPEN)] (2.22×10$^{-6}$ mol, S/C 12,500), 0.80 mg of sodium formate (11.5×10$^{-6}$ mol) and 0.100 g of (S)-1,1,1-trifluoro-2-propanol (0.89 mmol, 99.3% ee) as additive. The autoclave was sealed and the hydrogenation was run under stirring at 40° C. and 40×10$^5$ Pa of hydrogen. After 20 h the autoclave was vented and opened. Crude product (2.631 g, incl. additive) with 97.9% ee and 52.6% purity was isolated as a yellowish oil. Bulb-to-bulb distillation of the crude product (oven temperature: r.t. to 130° C., 1 atm) afforded 40% (corrected) of the title compound (1.667 g, incl. additive) as a colorless oil with 97.6% ee and 82.2% purity.

Example 15

(S)-1,1,1-Trifluoro-2-propanol

In an analogous manner to Example 14 but in the presence of 3.40 mg of [RuCl$_2$((S)-3,5-tPe-MeOBIPHEP)((R,R)-DPEN)] (2.22×10$^{-6}$ mol, S/C 12,500) instead of [RuCl$_2$((S)-3,5-tBu-MeOBIPHEP)((R,R)-DPEN)] as catalyst, the tile compound was isolated after bulb-to-bulb distillation in 78% yield (corrected) (2.679 g, incl. additive) with 98.7% ee and 96.4% purity.

Example 16

(S)-1,1,1-Trifluoro-2-propanol

In an analogous manner to Example 14 but in the presence of 3.35 mg of [RuCl$_2$((S)-3,5-tBu-4-MeO-MeOBIPHEP)((R,R)-DPEN)] (2.23×10$^{-6}$ mol, S/C 12,500) instead of [RuCl$_2$((S)-3,5-tBu-MeOBIPHEP)((R,R)-DPEN)] as catalyst, the tile compound was isolated after bulb-to-bulb distillation in 76% yield (corrected) (2.697 g, incl. additive) with 98.0% ee and 93.2% purity.

Example 16.2

(S)-1,1,1,-Trifluoro-2-propanol

In an analogous manner to Example 1.2 but in the presence of 32.7 mg of [RuCl$_2$((S)-DTBM-SEGPHOS)((R,R)-DPEN)] (10.5×10$^{-6}$ mol, S/C 20,000) instead of [RuCl$_2$((S)-3,5-tBu-MeOBIPHEP)((R,R)-DPEN)] as catalyst, the tile compound was isolated after bulb-to-bulb distillation in 88% yield (corrected) (20.90 g, incl. additive) with 98.8% ee and 98.9% purity.

Example 17

(S)-1,1,1-Trifluoro-2-propanol

In an analogous manner to Example 1 but in the presence of 17.27 mg of [RuCl$_2$((S)-3,5-tBu-MeOBIPHEP)(EN)] (13.67×10$^{-6}$ mol, S/C 2,000) instead of [RuCl$_2$((S)-3,5-tBu-MeOBIPHEP)((R,R)-DPEN)] as catalyst and 10.0 mg (0.144 mmol) instead of 0.8 mg of sodium formate, the tile compound was isolated after bulb-to-bulb distillation in 33% yield (corrected) (1.144 g, incl. additive) with 95.9% ee and 97.7% purity.

Example 18

(S)-1,1,1-Trifluoro-2-propanol

A 35-ml stainless steel autoclave was charged on air with 3.125 g of 1,1,1-trifluoroacetone (27.89 mmol), 2.90 mg of [RuCl$_2$((S)-3,5-Xyl-MeOBIPHEP)((R,R)-DPEN)] (12.05×10$^{-6}$ mol, S/C 2,300) and 3.80 mg of silver(I) acetate (22.5×10$^{-6}$ mol). The autoclave was sealed and the hydrogenation was run under stirring at 40° C. and 40×10$^5$ Pa of hydrogen. After 24 h the autoclave was vented and opened. Crude product (1.944 g) with 59.9% ee and 88.4% purity was isolated as a yellowish oil. Bulb-to-bulb distillation of the crude product (oven temperature: r.t. to 130° C., 1 atm) afforded 47% of the title compound (1.559 g) as a colorless oil with 95.8% ee and 95.1% purity.

Example 19

(S)-1,1,1-Trifluoro-2-propanol

In an analogous manner to Example 1 but in the presence of 19.35 mg of [RuCl$_2$((S)-3,5-tBu-MeOBIPHEP)((rac)-DPEN)] (13.67×10$^{-6}$ mol, S/C 2,000) instead of [RuCl$_2$((S)-3,5-tBu-MeOBIPHEP)((R,R)-DPEN)] as catalyst and 10.0 mg (0.144 mmol) instead of 0.8 mg of sodium formate, the tile compound was isolated after bulb-to-bulb distillation in 98% yield (corrected) (3.168 g, incl. additive) with 98.7% ee and >99.9% purity.

Example 20

(S)-1,1,1-Trifluoro-2-propanol

A 185-ml stainless steel autoclave was charged under argon in a glove box with 23.44 g of 1,1,1-trifluoroacetone (209.2 mmol), 14.81 mg of [RuCl$_2$((S)-3,5-tBu-MeOBIPHEP)((R,R)-DPEN)] (10.46×10$^{-6}$ mol, S/C 20,000), 75.00 mg of sodium formate (1.103 mmol) and 0.750 g of water as additive. The autoclave was sealed, the hydrogenation pressure set at 40×10$^5$ Pa and the hydrogenation run under stirring at 40° C. for 10 h and at 60° C. for 2 h. Then the autoclave was vented and opened. Crude product (24.23 g, incl. additive) with 99.2% ee and 99.5% purity was isolated as a yellowish oil. Distillation of the crude product (50° C., 15×10$^4$ Pa) afforded 95% of the title compound (23.41 g, incl. additive) as a colorless oil with 99.2% ee and 99.8% purity.

Example 21

(S)-1,1,1-Trifluoro-2-propanol

In an analogous manner to Example 1 but in the presence of 14.01 mg of [RuCl$_2$((S)-MeOBIPHEP)((R,R)-DPEN)] (13.67×10$^{-6}$ mol, S/C 2,000) instead of [RuCl$_2$((S)-3,5-tBu-MeOBIPHEP)((R,R)-DPEN)] as catalyst and 10.0 mg (0.144 mmol) instead of 0.8 mg of sodium formate, the tile compound was isolated after bulb-to-bulb distillation in 40% yield (1.800 g, incl. additive) with 98.0% ee and 74.8% purity.

Example 22

(S)-1,1,1-Trifluoro-2-propanol

In an analogous manner to Example 1 but in the presence of 13.60 mg of [RuCl$_2$((S)-TMBTP)((R,R)-DPEN)] (13.94×10$^{-6}$ mol, S/C 2,000) instead of [RuCl$_2$((S)-3,5-tBu-MeOBIPHEP)((R,R)-DPEN)] as catalyst and 10.0 mg (0.144 mmol) instead of 0.8 mg of sodium formate, the tile compound was isolated after bulb-to-bulb distillation in 32% yield (1.602 g, incl. additive) with 93.2% ee and 67.1% purity.

Asymmetric Hydrogenation of 1,1,1-Trifluoroacetone Using Ruthenium-Dichloro-Catalyst [RuCl$_2$((S)-3,5-tBu-MeOBIPHEP)((R,R)-DPEN)] under Noyori's Condition (for comparison)

Example 23

(S)-1,1,1-Trifluoro-2-propanol

A 35-ml stainless steel autoclave was charged on air with 1.225 g of 1,1,1-trifluoroacetone (10.93 mmol), 7.74 mg of [RuCl$_2$((S)-3,5-tBu-MeOBIPHEP)((R,R)-DPEN)] (5.47×10$^{-6}$ mol, S/C 2,000), 6.60 mg of potassium tert.-butylat (54.7×10$^{-6}$ mol) and 4 ml of 2-propanol. The autoclave was sealed and the hydrogenation was run under stirring at 40° C. and 40×10$^5$ Pa of hydrogen. After 24 h the autoclave was vented and opened. The crude reaction solution contained 50.3% (S)-1,1,1-trifluoro-2-propanol (solvent 2-propanol not integrated, GC method as described in Example 1) with 98.1% ee. Because of the minor boiling point difference of approx. 4-5° C. between (S)-1,1,1-trifluoro-2-propanol and the solvent 2-propanol, no solvent-free, pure (S)-1,1,1-trifluoro-2-propanol could be isolated via simple distillation.

Asymmetric Hydrogenation of 1,1,1-Trifluoroacetone Using Ruthenium-Hydrido-Catalysts

EXAMPLES 24-28

Example 24

(S)-1,1,1-Trifluoro-2-propanol

A 35-ml stainless steel autoclave was charged on air with 3.125 g of 1,1,1-trifluoroacetone (27.89 mmol) and 2.90 mg of [RuH(BH$_4$)((S)-MeOBIPHEP)((R,R)-DPEN)] (14.26×10$^{-6}$ mol, S/C 2,000). The autoclave was sealed and the hydrogenation was run under stirring at 40° C. and 40×10$^5$ Pa of hydrogen. After 24 h the autoclave was vented and opened. Crude product (2.068 g) with 94.3% ee and >99.9% purity was isolated as a yellowish oil. Bulb-to-bulb distillation of the crude product (oven temperature: r.t. to 130° C., 1 atm) afforded 53% of the title compound (1.674 g) as a colorless oil with 94.2% ee and >99.9% purity.

Example 25

(S)-1,1,1-Trifluoro-2-propanol

A 35-ml stainless steel autoclave was charged on air with 1.240 g of 1,1,1-trifluoroacetone (11.07 mmol) and 54.00 mg of [RuH(BH$_4$)((S)-3,5-Xyl-MeOBIPHEP)((R,R)-DPEN)] (52.7×10$^{-6}$ mol, S/C 200). The autoclave was sealed and the hydrogenation was run under stirring at 40° C. and 40×10$^5$ Pa of hydrogen. After 3 h the autoclave was vented and opened. 75% of crude product (0.960 g) with 92.4% ee and 98.9% purity was isolated as a yellowish oil.

Example 26

(S)-1,1,1-Trifluoro-2-propanol

A 35-ml stainless steel autoclave was charged on air with 1.240 g of 1,1,1-trifluoroacetone (11.07 mmol) and 54.00 mg of [RuH(BH$_4$)((S)-3,5-Xyl-MeOBIPHEP)((S,S)-DPEN)] (52.7×10$^{-6}$ mol, S/C 200). The autoclave was sealed and the hydrogenation was run under stirring at 40° C. and 40×10$^5$ Pa of hydrogen. After 3 h the autoclave was vented and opened. 76% of crude product (0.980 g) with 89.2% ee and >99.9% purity was isolated as a yellowish oil.

Example 27

(S)-1,1,1-Trifluoro-2-propanol

A 185-ml stainless steel autoclave was charged on air with 25.000 g of 1,1,1-trifluoroacetone (223.1 mmol) and 139.00 mg of [RuH(BH$_4$)((S)-3,5-iPr-MeOBIPHEP)((R,R)-DPEN)] (0.11 mmol, S/C 2,000). The autoclave was sealed and the hydrogenation was run under stirring at 40° C. and 20×10$^5$ Pa of hydrogen. After 20 h the autoclave was vented and opened. Crude product (23.754 g) with 97.5% ee and >99.9% purity was isolated as a yellowish oil. Vacuum distillation of the crude product (oven temperature: 55° C., 10$^4$ Pa) afforded 86% of the title compound (21.781 g) as a colorless oil with 97.4% ee and >99.9% purity.

Example 28

(S)-1,1,1-Trifluoro-2-propanol

A 35-ml stainless steel autoclave was charged on air with 3.125 g of 1,1,1-trifluoroacetone (27.89 mmol) and 10.00 mg of [RuH(BH$_4$)((S)-TMBTP)((R,R)-DPEN)] (10.9×10$^{-6}$ mol, S/C 2,500). The autoclave was sealed and the hydrogenation was run under stirring at 40° C. and 40×10$^5$ Pa of hydrogen. After 24 h the autoclave was vented and opened. Crude product (1.976 g) with 93.2% ee and 92.5% purity was isolated as a yellowish oil. Bulb-to-bulb distillation of the crude product (oven temperature: r.t. to 130° C., 1 atm) afforded 52% of the title compound (1.777 g) as a colorless oil with 93.3% ee and 92.7% purity.

Asymmetric Hydrogenation of 1,1,1-Trifluoroacetone Using Ruthenium-Hydrido-Catalyst [RuH(BH$_4$)((S)-3,5-Xyl-MeOBIPHEP)((R,R)-DPEN)] under Noyori's Condition (for Comparison)

Example 29

(S)-1,1,1-Trifluoro-2-propanol

A 35-ml stainless steel autoclave was charged on air with 1.250 g of 1,1,1-trifluoroacetone (11.16 mmol), 7.00 mg of [RuH(BH$_4$)((S)-3,5-Xyl-MeOBIPHEP)((R,R)-DPEN)] (5.58×10$^{-6}$ mol, S/C 2,000) and 4 ml of 2-propanol. The autoclave was sealed and the hydrogenation was run under stirring at 40° C. and 40×10$^5$ Pa of hydrogen. After 24 h the autoclave was vented and opened. The crude reaction solution contained 75.7% (S)-1,1,1-trifluoro-2-propanol (solvent 2-propanol not integrated, GC method as described in Example 1) with 92.1% ee. Because of the minor boiling point difference of approx. 4-5° C. between (S)-1,1,1-trifluoro-2-propanol and the solvent 2-propanol, no solvent-free, pure (S)-1,1,1-trifluoro-2-propanol could be isolated via simple distillation.

Synthesis of Ruthenium-Dichloro-Catalysts

EXAMPLES 30-40

Example 30

[RuCl$_2$((S)-3,5-tBu-MeOBIPHEP)((R,R)-DPEN)]

In analogy to R. Noyori et al. (*J. Am. Chem. Soc.* 1995, 117, 2675), a 100-ml 2-necked round-bottomed flask equipped with a reflux condenser was charged under an argon atmosphere with 1.378 g of (S)-3,5-tBu-MeOBIPHEP (1.336 mmol), 0.668 g of [RuCl$_2$(benzene)]$_2$ (1.336 mmol) and 55 ml DMF. The brown solution was stirred at 100° C. for 10 min. At r.t., 0.567 g of (R,R)-DPEN (2.671 mmol) were added and the brown solution stirred at r.t. for 6 days. The volatiles were removed by rotatory evaporation (10$^3$ Pa, 60° C.) and the residue dried under vacuum (100 Pa) at r.t. for 2 h. 55 ml of hexane were added to the residue and the formed suspension was stirred at r.t. for 10 min. The supernatant was removed by suction with a micro-filter candle and the filtrate was rotatory evaporated to dryness (2000 Pa, 45° C.). The crude product was digested in 10 ml of pentane for 30 min at 0° C. and the supernatant was filtered off (as described above) to yield 82% of the tile compound (1.558 g) as a yellow, crystalline solid. $^{31}$P NMR (121 MHz, CDCl$_3$): 49.5 ppm (s). MS: 1414.8 (M$^+$).

Example 30.2

[RuCl$_2$((S)-3,5-tBu-MeOBIPHEP)((R,R)-DPEN)]

In analogy to Example 30, a 20-1 two-necked round-bottomed flask equipped with a reflux condenser was charged under an argon atmosphere with 700.0 g of (S)-3,5-tBu-MeO-BIPHEP (678.6 mol), 339.4 g of [RuCl$_2$(benzene)]$_2$ (678.6 g) and 7.71 of DMF. The brown solution was stirred at 100° C. for 10 min. At r.t., 288.1 g of (R,R)-DPEN (1.357 mol) was added and the brown solution was stirred at r.t. for 3 h. After cooling the reaction mixture to 0-5° C., 7 l of water and 1 kg of dicalite speedex as a filter aid were added. The formed suspension was filtered off and the filter cake was washed with 21 l of water. Then, the cake was suspended in 7 l of methylene chloride at r.t. for 1 h. The suspension was filtered off and the filter cake washed with 3.5 l of methylene chloride. The combined filtrates were concentrated to a total volume of approx. 5 l. Then, 15 l of methanol were added and the resulting solution concentrated again to approx. 5 l to afford an orange suspension. The suspension was cooled to 0-5C and filtered. The filter cake was washed with 2 l of ice-cold methanol to yield after drying 83% of the tile compound (800.0 g) as an orange, crystalline solid. $^{31}$P NMR (121 MHz, CDCl$_3$): 49.5 ppm (s). MS: 1414.8 (M$^+$).

Example 31

[RuCl$_2$((S)-3,5-tBu-C3-Tuna-MeOBIPHEP)((R,R)-DPEN)]

In an analogous manner to Example 30, the title compound was synthesized (reaction time of 2 days) starting from 0.300 g of (S)-3,5-tBu-C3-Tuna-MeOBIPHEP (0.287 mmol) (prepared in analogy to X. Zhang et al, *J. Org. Chem.* 2000, 65, 6223), 0.108 g of [RuCl$_2$(benzene)]$_2$ (0.216 mmol) and 0.092 g of (R,R)-DPEN (0.433 mmol) in a yield of >99% (0.422 g) as a light brownish, crystalline solid. $^{31}$P NMR (121 MHz, CDCl$_3$): 50.9 ppm (s). MS: 1426.3 (M$^+$).

Example 32

[RuCl$_2$((S)-MeOBIPHEP)((R,R)-DPEN)]

In an analogous manner to Example 30, the title compound was synthesized (reaction time of 6 h) starting from 1.000 g of (S)-MeOBIPHEP (1.716 mmol), 0.429 g of [RuCl$_2$(benzene)]$_2$ (0.858 mmol) and 0.376 g of (R,R)-DPEN (1.716 mmol) in a yield of 81% (1.370 g) as a yellow, crystalline solid. $^{31}$P NMR (121 MHz, CDCl$_3$): 46.4 ppm (s). MS: 931.1 (M–Cl$^+$).

Example 33

[RuCl$_2$((S)-3,5-Xyl-MeOBIPHEP)((R,R)-DPEN)]

In an analogous manner to Example 30, the title compound was synthesized (reaction time of 6 h) starting from 0.405 g of (S)-3,5-Xyl-MeOBIPHEP (0.583 mmol), 0.146 g of [RuCl$_2$(benzene)]$_2$ (0.291 mmol) and 0.128 g of (R,R)-DPEN (0.583 mmol) in a yield of 91% (0.587 g) as a yellow, crystalline solid. $^{31}$P NMR (121 MHz, CDCl$_3$): 46.9 ppm (s). MS: 1043.3 (M–Cl$^+$).

Example 34

[RuCl$_2$((S)-3,5-Xyl-MeOBIPHEP)((S,S)-DPEN)]

In an analogous manner to Example 30, the title compound was synthesized (reaction time of 6 h) starting from 0.800 g of (S)-3,5-Xyl-MeOBIPHEP (1.150 mmol), 0.288 g of [RuCl$_2$(benzene)]$_2$ (0.576 mmol) and 0.244 g of (S,S)-DPEN (1.150 mmol) in a yield of 58% (0.715 g) as a yellow, crystalline solid. $^{31}$P NMR (121 MHz, CDCl$_3$): 45.3 ppm (s). MS: 1043.8 (M–Cl$^+$).

Example 35

[RuCl$_2$((S)-3,5-iPr-MeOBIPHEP)((R,R)-DPEN)]

In an analogous manner to Example 30 the title compound was synthesized (reaction time of 2 days) starting from 0.324 g of (S)-3,5-iPr-MeOBIPHEP (0.352 mmol), 0.088 g of [RuCl$_2$(benzene)]$_2$ (0.176 mmol) and 0.077 g of (R,R)-DPEN (0.352 mmol) in a yield of 86% (0.437 g) as a yellow, crystalline solid. $^{31}$P NMR (121 MHz, CDCl$_3$): 49.7 ppm (s). MS: 1267.5 (M–Cl$^+$).

Example 36

[RuCl$_2$ ((S)-3,5-tPe-MeOBIPHEP)((R,R)-DPEN)]

In an analogous manner to Example 30, the title compound was synthesized (reaction time of 7 days) starting from 0.850 g of (S)-3,5-tPe-MeOBIPHEP (0.743 mmol), 0.372 g of [RuCl$_2$(benzene)]$_2$ (0.744 mmol) and 0.316 g of (R,R)-DPEN (1.488 mmol) in a yield of 55% (0.626 g) as a yellow, crystalline solid. $^{31}$P NMR (121 MHz, CDCl$_3$): 48.4 ppm (s). MS: 1526.8 (M$^+$).

Example 37

[RuCl$_2$((S)-3,5-tBu-MeOBIPHEP)(EN)]

In an analogous manner to Example 30, the title compound was synthesized (reaction time of 24 h) starting from 1.000 g of (S)-3,5-tBu-MeOBIPHEP (0.970 mmol), 0.485 g of [RuCl$_2$(benzene)]$_2$ (0.970 mmol) and 0.131 ml of ethylendiamine (1.936 mmol) in a yield of 83.4% (1.022 g) as a yellow, crystalline solid. $^{31}$P NMR (121 MHz, CDCl$_3$): 47.7 ppm (s). MS: 1262.6 (M$^+$).

Example 38

[RuCl$_2$((S)-3,5-tBu-4-MeO-MeOBIPHEP)((R,R)-DPEN)]

In an analogous manner to Example 30, the title compound was synthesized (reaction time of 7 days) starting from 1.000 g of (S)-3,5-tBu-4-MeO-MeOBIPHEP (0.893 mmol), 0.447 g of [RuCl$_2$(benzene)]$_2$ (0.894 mmol) and 0.379 g of (R,R)-DPEN (1.785 mmol) in a yield of 54% (0.731 g) as a brownish, crystalline solid. $^{31}$P NMR (121 MHz, CDCl$_3$): 46.5 ppm (s). MS: 1502.7 (M$^+$).

Example 38.2

[RuCl$_2$((S)-DTBM-SEGPHOS)((R,R)-DPEN)]

In an analogous manner to Example 30, the title compound was synthesized (reaction time of 5 h) starting from 0.400 g of (S)-DTBM-Segphos (0.339 mmol), 0.170 g of [RuCl$_2$(benzene)]$_2$ (0.340 mmol) and 0.148 g of (R,R)-DPEN (0.676 mmol) in a yield of 98% (0.519 g) as a yellow, crystalline solid. $^{31}$P NMR (121 MHz, CDCl$_3$): 47.4 ppm (s). MS: 1562.7 (M$^+$).

Example 39

[RuCl$_2$((S)-TMBTP)((R,R)-DPEN)]

In an analogous manner to Example 30, the title compound was synthesized (reaction time of 1 h) starting from 2.000 g of (S)-TMBTP (3.380 mmol), 1.268 g of [RuCl$_2$(benzene)]$_2$ (2.535 mmol) and 1.076 g of (R,R)-DPEN (5.070 mmol) in a yield of >99.9% (3.608 g) as a yellow, crystalline solid. $^{31}$P NMR (121 MHz, CDCl$_3$): 46.6 ppm (s); MS: 976.1 (M$^+$).

Example 40

[RuCl$_2$((S)-3,5-tBu-MeOBIPHEP)((rac)-DPEN)]

In an analogous manner to Example 30, the title compound was synthesized (reaction time of 24 h) starting from 0.500 g of (S)-3,5-tBu-MeOBIPHEP (0.485 mmol), 0.242 g of [RuCl$_2$(benzene)]$_2$ (0.484 mmol) and 0.206 g of (rac)-DPEN (0.970 mmol) in a yield of 71% (0.490 g) as a brownish, crystalline solid. $^{31}$P NMR (121 MHz, CDCl$_3$): 49.5 ppm (s), 48.7 ppm (s). MS: 1414.7 (M$^+$).

Synthesis of Ruthenium-Hydrido-Catalysts
EXAMPLES 41-45

Example 41

[RuH(BH$_4$)((S)-MeOBIPHEP)((R,R)-DPEN)]

In analogy to R. Noyori et al. (*J. Am. Chem. Soc.* 2002, 124, 6508), a 200-ml 2-necked round-bottomed flask equipped with a reflux condenser was charged under an argon atmosphere with 1.500 g of [RuCl$_2$((S)-MeOBIPHEP)((R,R)-DPEN)] (1.463 mmol), 1.441 g of sodium borohydride (36.58 mmol), 30 ml of toluene and 30 ml of ethanol. The yellow solution was stirred at 65° C. for 10 min and at r.t. for 30 min. The suspension was concentrated to a volume of ca. 20 ml by rotatory evaporation (2000 Pa, 40° C.). 30 ml of toluene was added and the suspension filtered through a celite pad. The filtrate was evaporated to dryness (2000 Pa, 40° C.). The resulting crude product was digested in 80 ml of hexane at r.t. for 30 min. The supernatant was removed by suction with a micro-filter candle to yield 98% of the tile compound (1.388 g) as a white, crystalline solid. $^{31}$P NMR (121 MHz, C$_6$D$_6$): 87.5 ppm (d, J=41 Hz), 84.4 ppm (d, J=41 Hz). MS: 912.2 (M$^+$).

Example 42

[RuH(BH$_4$)((S)-3,5-Xyl-MeOBIPHEP)((R,R)-DPEN)]

In an analogous manner to Example 41, the title compound was synthesized starting from 0.800 g of [RuCl$_2$((S)-3,5-Xyl-MeOBIPHEP)((R,R)-DPEN)] (0.709 mmol) and 0.699 g of sodium borohydride (17.73 mmol) in a yield of 88% (0.638 g) as a white, crystalline solid. $^{31}$P NMR (121 MHz, C$_6$D$_6$): 88.1 ppm (d, J=41 Hz), 85.7 ppm (d, J=41 Hz). MS: 1009.4 (M−BH$_4^+$).

Example 43

[RuH(BH$_4$)((S)-3,5-Xyl-MeOBIPHEP)((S,S)-DPEN)]

In an analogous manner to Example 41, the title compound was synthesized starting from 1.000 g of [RuCl$_2$((S)-3,5-Xyl-MeOBIPHEP)((S,S)-DPEN)] (0.834 mmol) and 0.822 g of sodium borohydride (20.85 mmol) in a yield of 93% (0.795 g) as a white, crystalline solid. $^{31}$P NMR (121 MHz, C$_6$D$_6$): 88.0 ppm (d, J=41 Hz), 84.7 ppm (d, J=41 Hz). MS: 1009.4 (M−BH$_4^+$).

Example 44

[RuH (BH$_4$)((S)-3,5-iPr-MeOBIPHEP)((R,R)-DPEN)]

In an analogous manner to Example 41, the title compound was synthesized starting from 0.689 g of [RuCl$_2$((S)-3,5-iPr-MeOBIPHEP)((R,R)-DPEN)] (0.529 mmol) and 0.521 g of sodium borohydride (13.22 mmol) in a yield of >99% (0.690 g) as a yellowish, crystalline solid. $^{31}$P NMR (121 MHz, C$_6$D$_6$): 89.7 ppm (d, J=42 Hz), 84.5 ppm (d, J=42 Hz). MS: 1248.4 (M$^+$).

Example 45

[RuH(BH$_4$)((S)-TMBTP)((R,R)-DPEN)]

In an analogous manner to Example 41, the title compound was synthesized starting from 1.000 g of [RuCl$_2$((S)-TMBTP)((R,R)-DPEN)] (1.030 mmol) and 1.015 g of sodium borohydride (25.76 mmol) in a yield of 96% (0.909 g) as a brownish, crystalline solid. $^{31}$P NMR (121 MHz, C$_6$D$_6$): 86.1 ppm (d, J=40 Hz), 81.9 ppm (d, J=40 Hz). MS: 919.9 (M$^+$).

The invention claimed is:

1. A method for preparing an enantiomerically pure (S)-1,1,1-trifluoro-2-propanol by an asymmetric hydrogenation of 1,1,1-trifluoroacetone comprising hydrogenating 1,1,1-trifluoroacetone in the presence of a ruthenium phosphine complex catalyst represented by formula Ru(E)(E')(L)(A)

wherein E, E' are both chloro or E is hydrogen and E' is BH$_4$;
L is a chiral diphosphine ligand; and
A is an optionally chiral diamine
wherein hydrogenation occurs
in the absence of a solvent and
a) in the presence of a weak base, with or without an additive, when E and E' are both chloro or
b) in the absence of a base and an additive when E and E' are hydrogen and BH$_4$.

2. The method of claim 1, wherein the ruthenium phosphine complex catalyst is represented by formula Ru(Cl)$_2$(L)(A)

wherein
L is a chiral diphosphine ligand; and
A is an optionally chiral diamine
in the presence of a weak base, with or without an additive.

3. The method of claim 2, wherein the ruthenium phosphine complex catalyst is selected from the group consisting of catalysts of formulas 3, 3-1, 3-2, 3-3, 3-4, and all possible optical isomers (R,R), (S,S), (rac), (meso), (R), and (S) thereof:

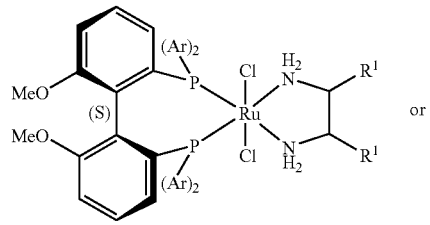

3

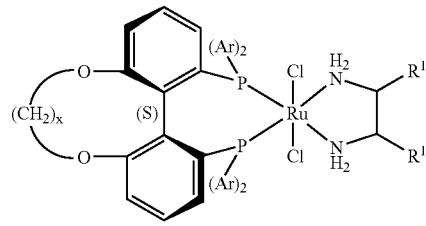

3-1

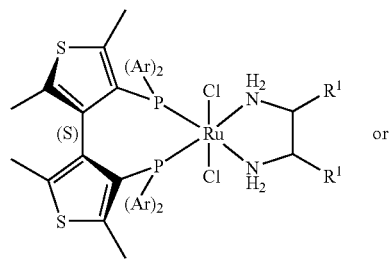

3-2

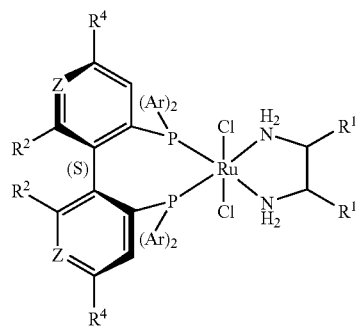

3-3

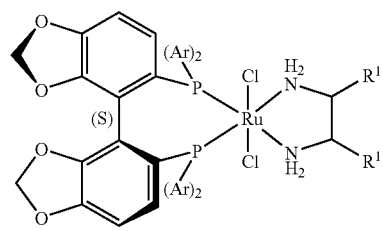

3-4 wherein
Ar is phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl group(s);
Z is N or C—$R^3$;
each $R^1$ is independently hydrogen, $C_{1-7}$-alkyl, cycloalkyl or aryl; or taken together form a —$(CH_2)_4$-bridge;
$R^2$ is $C_{1-7}$-alkyl, $C_{1-7}$-alkoxy, hydroxy or —OC(O)—$C_{1-7}$-alkyl;

$R^3$ and $R^4$ are each independently hydrogen, $C_{1-7}$-alkyl, $C_{1-7}$-alkoxy, halogen or di-$C_{1-7}$-alkylamino; or $R^2$ and $R^3$ or $R^3$ and $R^4$ which are attached to the same phenyl group, or both $R^2$ attached to different phenyl groups, taken together, are —X—$(CH_2)_n$—Y—; or —X—$(CF_2)$—X— wherein X is O or C(O)O, Y is O or N($C_{1-7}$-alkyl) and n is an integer from 1 to 6; or $R^2$ and $R^3$ together with the carbon atoms to which they are attached, form a naphthyl or tetrahydronaphthyl ring; and x is an integer from 1 to 6.

4. The method of claim 3, wherein the ruthenium phosphine complex catalyst is selected from the group consisting of catalysts of formulas 3, 3-1, 3-4, and all possible optical isomers (R,R), (S,S), (rac), (meso), (R), and (S) thereof:

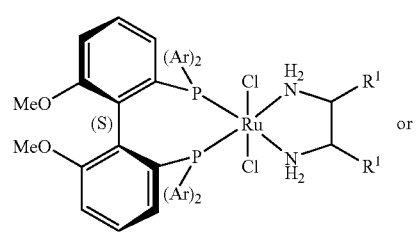

3

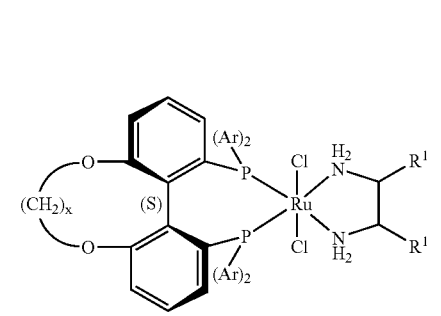

3-1

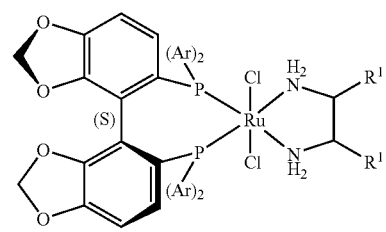

3-4 wherein
Ar is

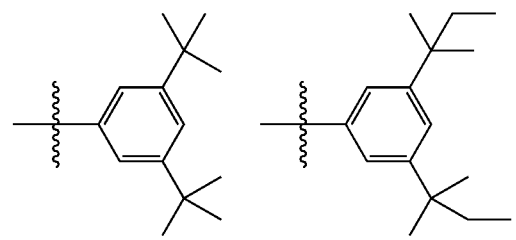

-continued

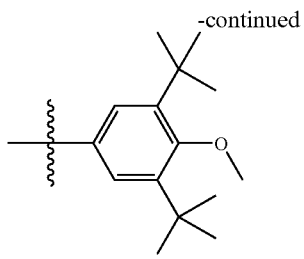

R[1] is phenyl; and
x is 2 or 3.

5. The method of claim 4, wherein the ruthenium phosphine complex catalyst is

3

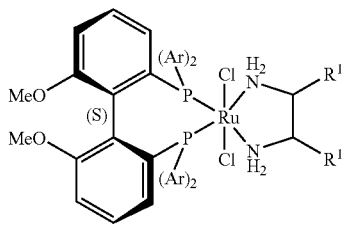

Ar is

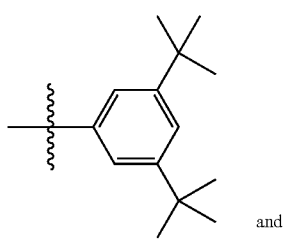

and

R[1] is phenyl, and the optical isomers (R,R), (S,S), (rac) and (meso) thereof.

6. The method of claim 2, wherein the weak base is selected from the group consisting of ammonium, transition metal, alkali metal and alkali earth metal salts of $HCOO^-$, $AcO^-$, $CF_3COO^-$, $tBuCOO^-$, $HCO_3^-$ $HSO_4^-$, $SO_4^{2-}$, $HSO_3^-$, $H_2PO_3^-$, $HPO_3^{2-}$ and phenolates selected from the group consisting of 2,4-dinitrophenolate.

7. The method of claim 6, wherein the weak base is selected from the group consisting of ammonium, transition metal, alkali metal and alkali earth metal salts of $HCOO^-$ and $HCO_3^-$.

8. The method of claim 2, wherein the weak base is present in an amount of 0.01-10 mol-% relative to 1,1,1-trifluoroacetone.

9. The method of claim 2, wherein the additives are water and/or 1,1,1-trifluoro-2-propanol.

10. The method of claim 9, wherein the additive is present in an amount of 0.1-50 wt.-% relative to 1,1,1-trifluoroacetone.

11. The method of claim 2, wherein the substrate and catalyst are present in a substrate-to-catalyst molar ratio (S/C) is 1,000-100,000.

12. The method of claim 11, wherein the substrate-to-catalyst molar ratio (S/C) is 10,000-30,000.

13. The method of claim 2, wherein the process is carried out at a temperature between about 20 and 80° C.

14. The method of claim 13, wherein the process is carried out at a temperature between about 40 and 60° C.

15. The method of claim 2, wherein the process is carried out at a pressure between about $5 \times 10^5$ and $100 \times 10^5$ Pa of hydrogen.

16. The method of claim 15, wherein the process is carried out at a pressure between about $40 \times 10^5$ and $80 \times 10^5$ Pa of hydrogen.

17. The method of claim 2, which process comprises hydrogenating 1,1,1-trifluoroacetone in the presence of a ruthenium phosphine complex catalyst represented by formula

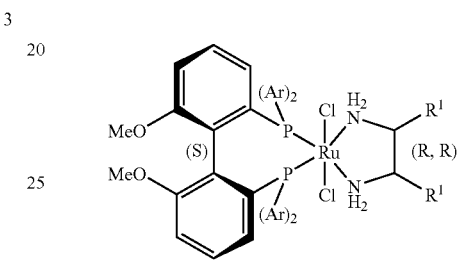

wherein
Ar is

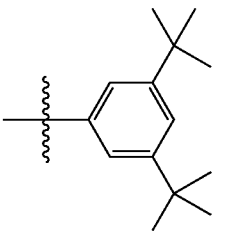

and

R[1] is phenyl in the presence of HCOONa in an amount of 0.04-0.5 mol-% relative to 1,1,1-trifluoroacetone and water in an amount of 1-3 wt-% relative to 1,1,1-trifluoroacetone, by a substrate-to-catalyst molar ratio (S/C) of 10,000-30,000, at 40-60° C. and $40 \times 10^5$-$80 \times 10^5$ Pa of hydrogen.

18. The method of claim 1 wherein the ruthenium phosphine complex catalyst is represented by formula Ru(H)(BH_4)(L)(A)

L is a chiral diphosphine ligand; and
A is an optionally chiral diamine
in the absence of a base and an additive.

19. The method of claim 18, wherein the ruthenium phosphine complex catalyst is selected from the group consisting of catalysts of formulas 4, 4-1, 4-2, 4-3, and all possible optical isomers (R,R), (S,S), (rac), (meso), (R), and (S) thereof:

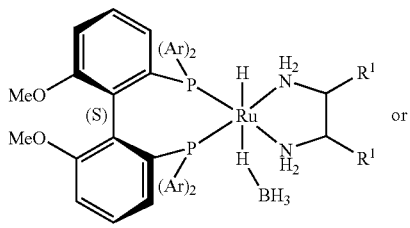

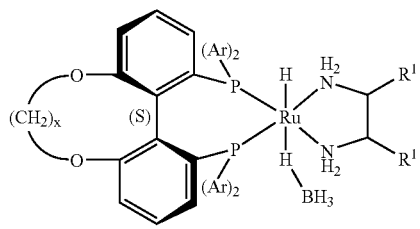

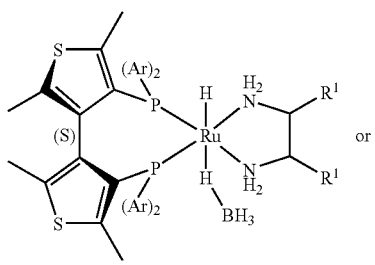

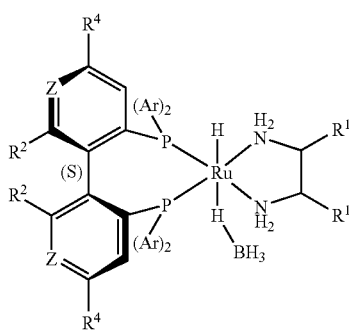

wherein

Ar is phenyl or phenyl substituted by one or more $C_{1-7}$-alkyl, $C_{1-7}$-alkoxy, phenyl, di-$C_{1-7}$-alkylamino, N-morpholino or tri-$C_{1-7}$-alkylsilyl group(s);

Z is N or C—$R^3$;

each $R^1$ is independently hydrogen, $C_{1-7}$-alkyl, cycloalkyl or aryl; or taken together form a —$(CH_2)_4$-bridge;

$R^2$ is $C_{1-7}$-alkyl, $C_{1-7}$-alkoxy, hydroxy or —OC(O)—$C_{1-7}$-alkyl;

$R^3$ and $R^4$ are each independently hydrogen, $C_{1-7}$-alkyl, $C_{1-7}$-alkoxy, halogen or di-$C_{1-7}$-alkylamino; or $R^2$ and $R^3$ or $R^3$ and $R^4$ which are attached to the same phenyl group, or both $R^2$ attached to different phenyl groups, taken together, are —X—$(CH_2)_n$—Y—; or —X—$(CF_2)$—X— wherein X is O or C(O)O, Y is O or N($C_{1-7}$-alkyl) and n is an integer from 1 to 6; and x is an integer from 1 to 6.

20. The method of claim 19, wherein the ruthenium phosphine complex catalyst is selected from the group consisting of catalysts of formulas 4, 4-1, and all possible optical isomers (R,R), (S,S), (rac), (meso), (R), and (S) thereof:

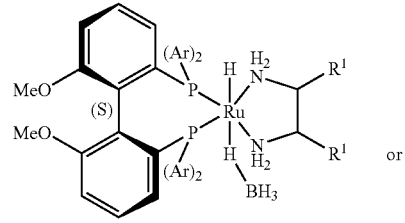

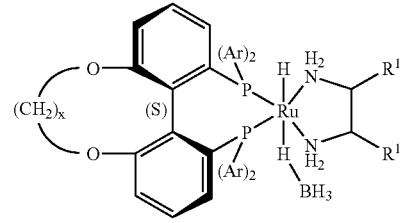

wherein

Ar is

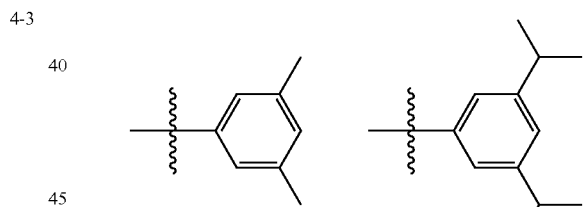

$R^1$ is phenyl; and x is 2 or 3.

21. The method of claim 20, wherein the ruthenium phosphine complex catalyst is

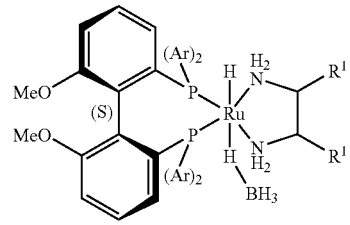

Ar is

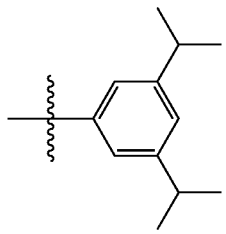 and

R[1] is phenyl, including the optical isomers (R,R), (S,S), (rac) and (meso).

22. The method of claim 18, wherein the substrate and catalyst are present in a substrate-to-catalyst molar ratio (S/C) is 1,000-50,000.

23. The method of claim 22, wherein the substrate-to-catalyst molar ratio (S/C) is 2,000-20,000.

24. The method of claim 18, wherein the process is carried out at a temperature between about 20 and 80° C.

25. The method of claim 24, wherein the process is carried out at a temperature between about 40 and 60° C.

26. The method of claim 18, wherein the process is carried out at a pressure between about $5 \times 10^5$ and $100 \times 10^5$ Pa of hydrogen.

27. The method of claim 26, wherein the process is carried out at a pressure between about $40 \times 10^5$ and $80 \times 10^5$ Pa of hydrogen.

28. The method of claim 18, which process comprises hydrogenating 1,1,1-trifluoroacetone in the presence of a ruthenium phosphine complex catalyst represented by formula

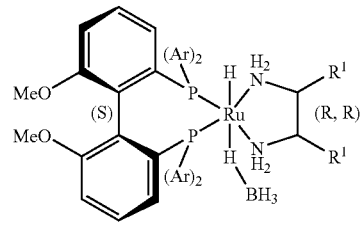

wherein
Ar is

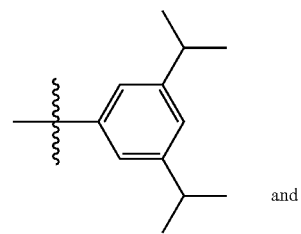 and

R[1] is phenyl without a base or additive by a substrate-to-catalyst molar ratio (S/C) of 2,000-20,000, at 40-60° C. and $40 \times 10^5$-$80 \times 10^5$ Pa of hydrogen.

\* \* \* \* \*